United States Patent
Chen et al.

(10) Patent No.: US 7,391,524 B1
(45) Date of Patent: Jun. 24, 2008

(54) SYSTEM AND METHOD FOR EFFICIENT CHARACTERIZATION OF DIFFRACTING STRUCTURES WITH INCIDENT PLANE PARALLEL TO GRATING LINES

(75) Inventors: Shuqiang Chen, Sunnyvale, CA (US); Guoguang Li, Fremont, CA (US)

(73) Assignee: n&k Technology, Inc., San Jose, CA (US)

( * ) Notice: Subject to any disclaimer, the term of this patent is extended or adjusted under 35 U.S.C. 154(b) by 407 days.

(21) Appl. No.: 10/940,243

(22) Filed: Sep. 13, 2004

(51) Int. Cl.
*G01B 11/14* (2006.01)
*G01B 11/02* (2006.01)

(52) U.S. Cl. ............... 356/625; 356/634; 356/635; 356/636

(58) Field of Classification Search ......... 356/601–625, 356/634–636; 250/559.22, 559.24, 550; 702/76; 438/16
See application file for complete search history.

(56) References Cited

U.S. PATENT DOCUMENTS

| | | | |
|---|---|---|---|
| 5,337,146 A * | 8/1994 | Azzam | 356/367 |
| 5,963,329 A | 10/1999 | Conrad et al. | 356/372 |
| 6,451,700 B1 * | 9/2002 | Stirton et al. | 438/695 |
| 6,483,580 B1 | 11/2002 | Xu et al. | 356/300 |
| 6,713,753 B1 | 3/2004 | Rovira et al. | 250/225 |
| 6,775,015 B2 * | 8/2004 | Bischoff et al. | 356/636 |
| 6,867,862 B2 * | 3/2005 | Nikoonahad | 356/340 |
| 6,867,866 B1 * | 3/2005 | Chang et al. | 356/446 |
| 6,891,626 B2 * | 5/2005 | Niu et al. | 356/625 |
| 6,898,537 B1 * | 5/2005 | McGahan | 702/76 |
| 6,919,964 B2 * | 7/2005 | Chu | 356/601 |
| 7,029,110 B2 * | 4/2006 | Takao et al. | 347/100 |
| 7,139,128 B2 * | 11/2006 | Smith et al. | 359/572 |

OTHER PUBLICATIONS

M. G. Moharam et al., "Stable implementation of the rigorous coupled-wave analysis for surface-relief gratings: enhanced transmittance matrix approach," J. Opt. Soc. Am. A. vol. 12, No. 5, May 1995, pp. 1077-1086.

(Continued)

*Primary Examiner*—Sang Nguyen
(74) *Attorney, Agent, or Firm*—Lumen Patent Firm, Inc.

(57) ABSTRACT

A system and a method for optical characterization of a symmetric grating illuminated at off-normal incident angle are provided, where the plane of incidence is parallel to the grating lines. In this case corresponding positive and negative diffraction orders have the same intensity and phase. Several approaches for exploiting this symmetry are given. The first approach is a symmetric rigorous coupled wave analysis (SRCWA) adapted to the symmetric case, which accounts for N positive and N negative diffraction orders with M=N+1 space harmonics, without approximation. Various approximation methods are also given. Approximate versions of the RCWA (or SRCWA) can be developed by neglecting polarization coupling for small angles of incidence. A normal incident angle calculation can be used to approximate a situation with a small angle of incidence. Refinements to this approximation include revision of grating depth or refractive indices to improve accuracy. Methods other than the RCWA can also be symmetry simplified according to the invention.

35 Claims, 12 Drawing Sheets

OTHER PUBLICATIONS

M. G. Moharam et al., "Formulation for stable and efficient implementation of the rigorous coupled-wave analysis of binary gratings," J. Opt. Soc. Am. A, vol. 12, No. 5, May 1995, pp. 1068-1076.

William A. McGahan, "Measurement of Diffracting Structures Using One-Half of the Non-Zero Diffracted Orders," U.S. Appl. No. 09/844,599, filed Apr. 27, 2001.

Christopher J. Raymond, "Asymmetric line profile measurement using angular scatterometry," Proc. SPIE vol. 4344, 2001, pp. 436-446.

Lifeng Li, "A modal analysis of lamellar diffraction gratings in conical mountings," Journal of Modern Optics, 1993, vol. 40, No. 4 pp. 553-573.

* cited by examiner

SYSTEM AND METHOD FOR EFFICIENT CHARACTERIZATION OF DIFFRACTING STRUCTURES WITH INCIDENT PLANE PARALLEL TO GRATING LINES

FIELD OF THE INVENTION

This invention relates to optical characterization of patterned structures.

BACKGROUND

Manufacturing processes for producing products usually rely on quantitative measurements to provide information required for process control. Such measurements can be made on the final product, and/or on intermediate stages of the product within the manufacturing process, and/or on tools/fixtures used in the manufacturing process. For example, in semiconductor chip fabrication, measurements can be performed on finished chips (i.e., final product), on a wafer patterned with a photoresist (i.e., intermediate stage), or on a mask (i.e., a tool or fixture). Frequently, as in the case of semiconductor chip fabrication, these measurements are performed on structures having small dimensions. Furthermore, it is highly desirable to perform process control measurements quickly and non-destructively, in order to ensure a minimal impact on the process being controlled. Since optical measurements can be performed quickly, tend to be non-destructive, and can be sensitive to small features, various optical process control measurements have been developed.

Optical process control measurements can often be regarded as methods for measuring parameters of a pattern. For example, a pattern can be a periodic one-dimensional grating of lines on the surface of a wafer, and the parameters to measure can be line width, line spacing and depth of the grating. To measure these parameters, an optical response of the pattern is measured. For example, reflectance as a function of wavelength can be measured. Typically, the optical response will depend on the parameter (or parameters) of interest in a complicated way such that direct parameter extraction from measured data is impractical. Instead, a mathematical model is typically constructed for the pattern, having the parameters of interest as variables. Within the model, a modeled optical response is calculated corresponding to the measured optical response. The parameters of interest are then, determined by adjusting the variables to fit the modeled response to the measured response. Various optical process control measurements differ depending on the measured response(s), and on the kind of mathematical model employed.

A commonly-employed modeling approach for grating diffraction, known as the rigorous coupled wave analysis (RCWA), is described by Moharam et al. in Journal of the Optical Society of America (JOSA), A12, n5, p 1068-1076, 1995. The RCWA was first introduced by K. Knop in JOSA, v68, p 1206, 1978, and was later greatly improved by Moharam et al. in the above-referenced article. Some implementations of the RCWA are described in U.S. Pat. Nos. 6,590,656 and 6,483,580 assigned to KLA-Tencor, U.S. Pat. No. 5,963,329 assigned to IBM, and U.S. Pat. No. 5,867,276 assigned to Bio-Rad.

Since a grating is periodic, grating-diffracted optical fields can be expressed as a superposition of space harmonics, each space harmonic having a different spatial period. Although an infinite number of space harmonics is required for an exact solution of the grating diffraction problem, use of a finite number M of space harmonics provides an approximate solution suitable for numerical solution on a computer. Increasing M increases accuracy, but requires more computation time, while decreasing M decreases computation time, but provides reduced accuracy. The M space harmonics each correspond to a diffraction order, so in a typical case where positive diffraction orders 1 through N, negative diffraction orders −1 through −N, and zero order diffraction are to be included in a calculation, we have $M=2N+1$. The RCWA is generally based on such a finite M approximation to the grating diffraction problem.

The time required to perform numerical RCWA calculations is dominated by matrix operations having a calculation time on the order of $M^3$, so simply increasing M to provide increased accuracy is not always a reasonable approach in practice. Accordingly, various special cases have been considered in the literature where calculation time can be reduced compared to a more general case without reducing accuracy.

For example, in the above-referenced article by Moharam et al., planar diffraction is identified as a special case of conical diffraction. In planar diffraction, the plane of incidence of the light on the grating is perpendicular to the grating lines, while in conical diffraction, the plane of incidence makes an arbitrary angle with respect to the grating lines. Moharam et al. show that a planar diffraction calculation for N orders requires less than half the computation time of a conical diffraction calculation for N orders. The reason for this difference is that there is no coupling between TE and TM polarized waves in planar diffraction, while TE and TM polarized waves are generally coupled in conical diffraction. Moharam et al. also indicate that for planar diffraction from a symmetric grating, the matrices to be processed take on special forms (i.e., symmetric for lossless gratings and Hermitian for lossy gratings), which can reduce computation time. Thus, a planar diffraction geometry has typically been used for grating characterization based on RCWA calculations.

Another special case for characterization with RCWA calculations which has been considered is normal incident angle illumination of a symmetric grating. For example, U.S. patent application Ser. No. 09/844,559, entitled "Measurement of Diffracting Structures Using One-Half of the Non-Zero Diffracted Orders", and assigned to Nanometrics, considers this case. This case is especially simple, since illumination with normal incident angle is a special case of planar diffraction (i.e., the polarization coupling of conical diffraction does not occur), and illumination with normal incident angle on a symmetric grating leads to symmetric positive and negative diffraction orders. Thus N positive orders, N negative orders and the zero order can be accounted for in this case with only $M=N+1$ space harmonics. To accomplish this, a specialized RCWA assuming normal incident angle with a symmetric grating is derived from the standard RCWA.

However, the approach of U.S. patent application Ser. No. 09/844,559 requires illumination with normal incident angle on the grating, which leads to practical difficulties. For example, in the common case where the response of interest is a zero order reflection, normal incident angle illumination requires separation of the incident light from the zero order reflected light. Providing such separation (e.g., with a beam splitter) requires additional optical element(s), which undesirably increases system complexity.

Illumination of a grating at off-normal incidence with a plane of incidence parallel to the grating lines is considered by Raymond et al., in Proc. SPIE v4344 pp. 436-446 2001. However, Raymond et al., is concerned with characterizing asymmetric grating structures and accordingly does not consider simplifications made possible by symmetry. Raymond et al. also consider measurement of the zero order reflectance vs. angle, which requires a mechanical scanning arrangement to vary the angle. In contrast, measuring the zero order reflectance vs. wavelength (i.e., a spectral response) can be done without moving parts. Thus an object of the invention is to provide a method of characterizing a non-normally illuminated grating using an analysis having a symmetry-reduced calculation time.

SUMMARY

The present invention provides methods and systems for optical characterization of a symmetric grating illuminated at an off-normal angle of incidence $\theta$, where the plane of incidence is parallel to the grating lines. Diffraction in this case is symmetric conical diffraction, since corresponding positive and negative diffraction orders have the same intensity.

Several approaches for exploiting this symmetry are given in the following description. The first approach is the symmetric RCWA (SRCWA), which accounts for N positive and N negative diffraction orders and the zero order with M=N+1 space harmonics. As a result of this simplification, reduced matrices can be used, having dimension N+1 (instead of the usual 2N+1), which significantly reduces computation time. More specifically, the matrix eigenvalue equation reduces from a single 2N+1 dimension problem to two N+1 dimension problems. The boundary conditions reduce from a 4(2N+1) dimension problem to a 4(N+1) dimension problem, which can be further reduced to four 2(N+1) problems. With this simplification, the calculation will be faster than for the case of planar diffraction (which generally has a 2N+1 dimension eigenvalue problem and a 2(2N+1) dimension boundary conditions). The SRCWA does not entail any approximation.

Symmetric conical diffraction also lends itself to various approximation methods. For example, when the angle of incidence is small (i.e., less than about 9 degrees), approximate versions of the RCWA (or SRCWA) can be developed by neglecting polarization coupling. Application of this simplification to the SRCWA leads to a single N+1 dimension eigenvalue problem and four N+1 dimension boundary condition problems. Since these approximations are polarization dependent, s and p polarization are treated separately in the following description.

Another category of approximation methods is based on the use of a normal incident angle calculation to approximate a situation with a small angle of incidence. Refinements of the normal incident angle approximation include the use of revised grating depths to improve accuracy, and the use of revised indices to improve accuracy.

The effect of beam divergence can also be approximately accounted for, by revising depths or indices in an otherwise conventional planar diffraction calculation to simplify the calculation for off-axis plane wave beam components which are not exactly in the parallel plane of incidence.

The matrix reduction of the SRCWA is generally applicable to any of these approximation methods to further reduce calculation time. The invention is applicable to single-layer gratings and to multi-layer gratings. However, the grating must be symmetric (or approximately symmetric), such that it has even symmetry about a reflection plane parallel to the grating lines. Simple binary gratings are always symmetric in this sense.

Calculation methods other than the RCWA can also be simplified according to the invention for the case where the plane of incidence is parallel to the grating lines.

By reducing calculation time according to the invention, improved optical characterization systems are also provided.

DETAILED DESCRIPTION

The following detailed description includes a mathematical development of various RCWA-related calculation methods suitable for use with a symmetric conical diffraction geometry. This development includes a general development of the SRCWA (section 1a), approximations suitable for symmetric conical diffraction at small angles of incidence (sections 1b and 1c), and an extension of preceding results to multilayer gratings (section 1d). Following the mathematical development, various examples are given.

1) MATHEMATICAL DEVELOPMENT

Figure 1:
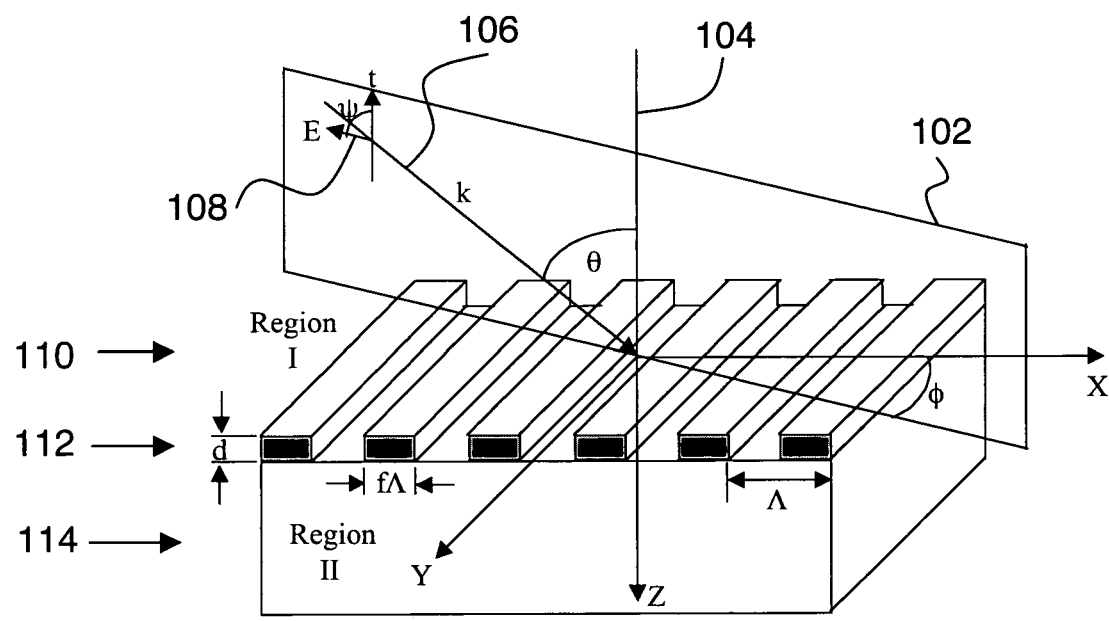
FIG. 1 shows general grating diffraction geometry.

FIG. 1 shows the geometry for grating diffraction. A grating 112 separates region I (110) from region II (114). Grating 112 has a period $\Lambda$, and has ridges of width $f\Lambda$ and grooves of width $(1-f)\Lambda$, where f (0<f<1) is a filling fraction. Grating 112 has a depth d and lies in the X-Y plane as shown. Thus the Z-axis is a surface normal. The lines of grating 112 are parallel to the Y axis. Light having a k vector 106 is incident on grating 112 from region I. A plane of incidence 102 is defined by k vector 106 and surface normal 104. The angle between plane of incidence 102 and the X axis is $\phi$, as shown. The angle of incidence of light on the grating is $\theta$, as shown. The angle the electric field vector 108 of the incident light makes with respect to the plane of incidence is $\psi$, as shown.

In the following development, it will be convenient to discuss polarization in terms of the relation between the electric field vector and the grating lines. More specifically, in "TE mode" the optical electric field has no X component on FIG. 1 and in "TM mode" the optical electric field has no Y component on FIG. 1. For example, if φ=0, then TE mode corresponds to s-polarized light and TM mode corresponds to p-polarized light. If φ=π/2, then TE mode corresponds to p-polarized light and TM mode corresponds to s-polarized light. Here s and p polarization is perpendicular and parallel, respectively, to the plane of incidence. We consistently use "TE" and "TM" to refer to polarization relative to the grating lines as indicated above, and "s" and "p" to refer to polarization with respect to the plane of incidence.

A commonly considered special case in the literature is the case φ=0, often called "planar diffraction". Note that planar diffraction has a plane of incidence that is normal to the grating lines. In contrast, the following development is mainly concerned with the case φ=π/2, referred to herein as "symmetric conical diffraction" and/or as having a plane of incidence "parallel to the grating lines".

1a) Symmetric RCWA (SRCWA, φ=π/2, θ Arbitrary)

Figure 2A:
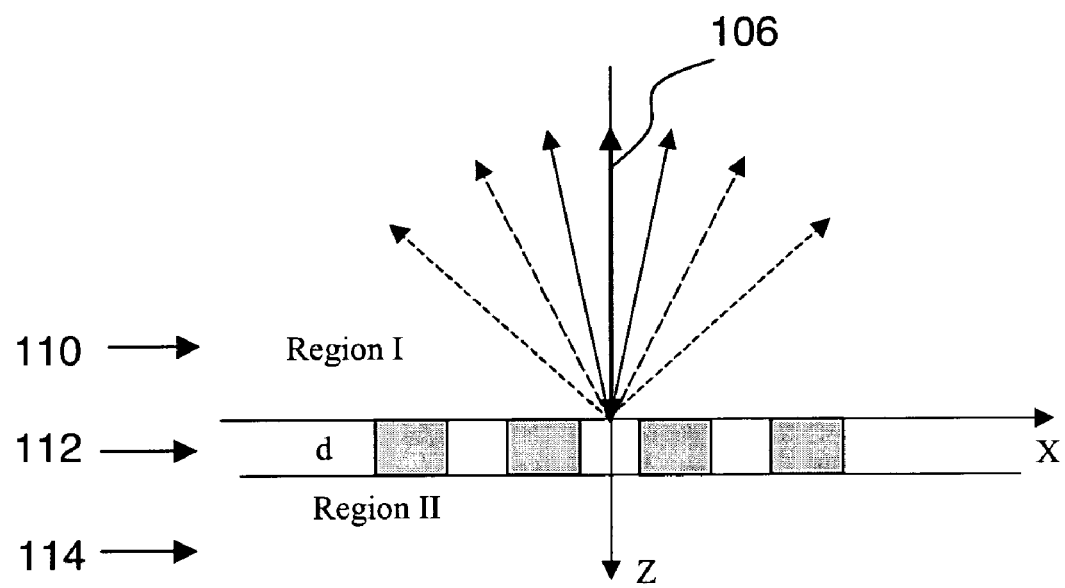
FIGS. 2a and 2b show diffraction geometry for symmetric conical diffraction.
Figure 2B:
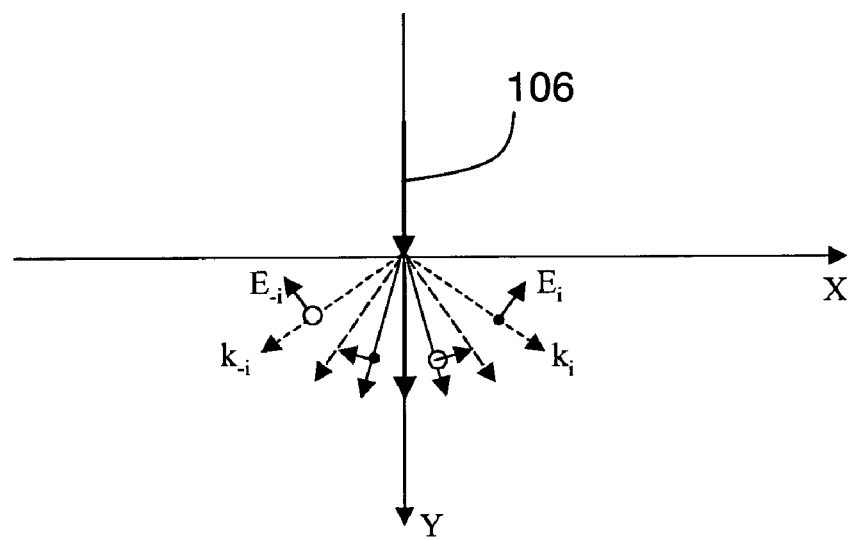

FIG. 2a shows an end view (i.e., along the Y axis of FIG. 1) of symmetric conical diffraction with φ=π/2. Several reflected diffraction orders are shown in region I of FIG. 2a. Generally, there are also transmitted diffraction orders in region II, but these are not shown on FIG. 2a. FIG. 2b shows a corresponding top view (i.e., along the Z axis of FIG. 1) of symmetric conical diffraction with φ=π/2.

Appendix A provides results following the development of Moharam et al. for the symmetric conical diffraction case. However, the matrix eigenvalue problems given in Appendix A (i.e., Eqs. A11) have dimension 2N+1 for N positive and N negative diffraction orders. For φ=π/2, the diffraction problem is symmetric, as schematically indicated on FIG. 2. More specifically, the amplitude and phase of the ith order diffracted wave is same as that of the −ith order diffracted wave. In the following development, this symmetry between positive and negative diffraction orders is exploited to reduce the dimensionality of the matrix eigenvalue problem corresponding to Eqs. A11 to N+1 for N positive and N negative symmetric diffraction orders.

Equations A11 can be expressed in component form as follows:

$$\frac{\partial^2 U_{xi}}{\partial z'^2} = \frac{k_y^2}{k_0^2} U_{xi} + \sum_{p=-N}^{N} A_{i,p} U_{xp} \quad (1)$$

$$\frac{\partial^2 S_{xi}}{\partial z'^2} = \frac{k_y^2}{k_0^2} S_{xi} + \sum_{p=-N}^{N} \sum_{j=-N}^{N} B_{i,j} \cdot E_{j,p} S_{xp}$$

$$i = -N, \ldots -1, 0, 1, \ldots N.$$

Since the grating is symmetric in −x and x direction, the amplitude of the field components of the positive and negative diffraction orders will also be symmetric. So we can set $U_{xi}=U_{x(-i)}$, $S_{xi}=S_{x(-i)}$, in Eq. 1 which gives $$\frac{\partial^2 U_{xi}}{\partial z'^2} = \frac{k_y^2}{k_0^2} U_{xi} + A_{i,0} U_{x0} + \sum_{p=1}^{N} (A_{i,p} + A_{i,-p}) U_{xp}, \quad (2)$$

$$i = 0, \ldots N$$

$$\frac{\partial^2 S_{xi}}{\partial z'^2} = \frac{k_y^2}{k_0^2} S_{xi} + \sum_{j=-N}^{N} B_{i,j} \left( E_{j,0} S_{x0} + \sum_{p=1}^{N} (E_{j,p} + E_{j,-p}) S_{xp} \right),$$

$$i = 0, \ldots N$$

Eqs. 2 can be expressed as $$\frac{\partial^2 U_{xi}}{\partial z'^2} = \frac{k_y^2}{k_0^2} U_{xi} + \sum_{p=0}^{N} A_{i,p}^r U_{xp} \quad (3)$$

$$\frac{\partial^2 S_{xi}}{\partial z'^2} = \frac{k_y^2}{k_0^2} S_{xi} + \sum_{j=-N}^{N} B_{i,j} \sum_{p=0}^{N} E_{i,p}^r S_{xp}$$

$$i = 0, 1, \ldots N,$$

by defining reduced matrices $A^r$ and $E^r$ having elements $$A_{i,p}^r = \begin{cases} A_{i,0}, & p = 0 \\ A_{i,p} + A_{i,-p}, & p \neq 0 \end{cases}, E_{i,p}^r = \begin{cases} E_{i,0}, & p = 0 \\ E_{i,p} + E_{i,-p}, & p \neq 0 \end{cases}. \quad (4)$$

The second equation of Eqs. (3) can be written as:

$$\frac{\partial^2 S_{xi}}{\partial z'^2} = \frac{k_y^2}{k_0^2} S_{xi} + \sum_{J=0}^{N} B_{i,j}^r \sum_{p=0}^{N} E_{j,p}^r S_{xp}, i = 0, 1, \ldots N \quad (5)$$

by defining a reduced matrix $B^r$ which is related to B the same way $A^r$ and $E^r$ are related to A and E in Eqs. 4. In Eq. 5, we recognize a matrix product of $B^r$ and $E^r$. More generally, a reduced matrix product is the product of the reduced factors (e.g., $B^r \cdot E^r = (BE)^r$). So Eqs. 3 can be expressed as:

$$\left[ \frac{\partial^2 U_x}{\partial z'^2} \right] = \left[ \frac{k_y^2}{k_0^2} I^r + A^r \right] U_x \quad (6)$$

$$\left[ \frac{\partial^2 S_x}{\partial z'^2} \right] = \left[ \frac{k_y^2}{k_0^2} I^r + B^r e^r \right] S_x$$

where $I^r$ is the identity matrix with dimension N+1. Eqs. 6 (having dimension N+1) are equivalent to Eqs. 1 (having dimension 2N+1), thus providing an explicit demonstration of reduced matrix size by exploiting symmetry. Similarly, boundary conditions as given by Eqs. A14, A15, and A18 can be replaced with their reduced equivalents, with all matrices replaced by their reduced matrices. In this way, the dimension of the boundary condition equations is reduced from 4(2N+1) to 4(N+1).

With the reduced dimension, we have calculated several examples. All of the results are exactly same as those from the full-size matrix, as one would expect. The calculation is much faster especially for large matrices, since the calculation time should scales roughly as dimension cubed when matrix floating point operation dominate the calculation time. The following table shows a comparison of calculation times between full matrices with parallel incident plane (i.e., $\phi=\pi/2$), full matrices with normal incident plane (i.e., $\phi=0$) and reduced matrices with parallel incident plane. The example is for a Si/Air binary grating with 9 degree incident angle and TE mode having a period $\Lambda=0.8$ μm, a depth d=1 μm and a line fraction f=0.4 on a Si substrate.

TABLE 1

Relative timing results

| # of nonzero diffraction orders retained | Parallel incident plane (full matrices) | Normal incident plane (full matrices) | Parallel incident plane (reduced matrices) | Parallel incident plane (Small angle approach) |
|---|---|---|---|---|
| 10 | 45(sec) | 24.3(sec) | 21(sec) | 8.7(sec) |
| 15 | 80.2(sec) | 46.8(sec) | 36.1(sec) | 12.2(sec) |
| 20 | 156(sec) | 86.2(sec) | 61(sec) | 17.6(sec) |
| 30 | 386.9(sec) | 229(sec) | 135(sec) | 32.8(sec) |

The table shows that the calculation is much faster for a given number N of nonzero diffraction orders with reduced matrices (matrix size N+1) than with full matrices (matrix size 2N+1), especially as N increases. The results in the rightmost column are timing results for small angle approximations to be discussed in the following sections, showing a significant further reduction in calculation time. The calculation is made with Matlab® on a Pentium 4, 1.8 GHz PC. The time improvement factor is typically even larger if a lower-level programming language such as C is used for the calculations. These timing results demonstrate the main advantage of the reduced matrix calculation.

In some cases, further reduction of the SRCWA calculation time is desired. The following two sections present approximate forms of the SRCWA which further reduce computation time and provide good approximations to the rigorous SRCWA for small angles of incidence (e.g., θ less than about 9 degrees). These approximations are developed separately for TE mode and TM mode.

From Appendix A, the field in the grating region $E_{gx}$, $E_{gy}$, $H_{gx}$ and $H_{gy}$ is given by $$\left.\begin{array}{l} E_{gx} = \sum_i S_{xi}(z)\exp[-j(k_{xi}x + k_y y)] \\ E_{gy} = \sum_i S_{yi}(z)\exp[-j(k_{xi}x + k_y y)] \\ H_{gx} = -j(\varepsilon_0/\mu_0)^{\frac{1}{2}} \sum_i U_{xi}(z)\exp[-j(k_{xi}x + k_y y)] \\ H_{gy} = -j(\varepsilon_0/\mu_0)^{\frac{1}{2}} \sum_i U_{yi}(z)\exp[-j(k_{xi}x + k_y y)] \end{array}\right\} \quad (7)$$

1b) TE Mode ($\phi=\pi/2$, Small θ)

In this case, $\psi=0$. In the grating region, Eq. A7 can be written as $$k_0^2 \varepsilon(x) H_{gx} = \frac{\partial^2 H_{gy}}{\partial x \partial y} - \frac{\partial^2 H_{gx}}{\partial y^2} - j\omega\varepsilon_0\varepsilon(x)\frac{\partial E_{gy}}{\partial z}. \quad (8)$$

From Eqs. 7 and A8, we have $$k_0^2 \sum_i U_{xi} \sum_h \varepsilon_h \exp[-jk_{x,i+h}x]$$

$$= k_0^2 \sum_i U_{xi}\exp(-jk_{xi}x) - k_y \sum_i k_{xi} U_{yi}\exp(-k_{xi}x) +$$

$$\sum_i \frac{\partial S_{yi}}{\partial z} \sum_h \varepsilon_h \exp(-jk_{x,h+i}x).$$

By comparing the amplitude for the same harmonic order and changing $$h + i \to i, h \to i - p, \sum_{i-p} \to \sum_p,$$

we find:

$$k_0^2 \sum_p U_{xp}\varepsilon_{i-p} = k_y^2 U_{xi} - k_y k_{xi} U_{yi} + k_0 \sum_i \frac{\partial S_{yi}}{\partial z}\varepsilon_{i-p}. \quad (10)$$

Similarly, from the second of Eqs. A7, we get $$k_0^2 \varepsilon(x) E_{gy} = \frac{\partial^2 E_{gx}}{\partial x \partial y} - \frac{\partial^2 E_{gy}}{\partial x^2} - j\omega\mu_0 \frac{\partial H_{gx}}{\partial z} \quad (11)$$

Application of the procedure of Eqs. 9 and 10 to Eq. 11 gives $$k_0^2 \sum_p S_{yp}\varepsilon_{i-p} = -k_y k_{xi} S_{xi} + k_{xi}^2 S_{yi} + k_0 \frac{\partial U_{xi}}{\partial z}. \quad (12)$$

For the incident beam normal to the grating (i.e., θ=0), the only components of the field are $S_{yi}$ and $U_{xi}$. For small incident angles, these are still the main field components. We assume that the ith order of magnetic field is within the plane defined by the k vector of the ith order diffraction wave and its projection into the x-y plane, and the same order electric field is perpendicular to the k vector and magnetic field. In this case, $U_{xi}$ has the same phase as $U_{yi}$, while $S_{xi}$ and $S_{yi}$ have opposite phases, and we have:

$$\frac{U_{yi}}{U_{xi}} = -\frac{S_{xi}}{S_{yi}} = \left\{\begin{array}{ll} 0, & i=0 \\ \tan\varphi_i, & i \neq 0 \end{array}\right\} == \operatorname{Tan}\varphi_i \quad (13)$$

where $\tan \phi_i$ is defined in Eq. A5. The point of this approximation is to simplify the calculation by neglecting the polarization coupling inherent in symmetrical conical diffraction. The error introduced by this approximation is small for small incident angles.

Eqs. 10 and 12 can be written as $$\sum_p \frac{\partial S_{yp}}{\partial z'}\varepsilon_{i-p} = -\frac{k_y^2}{k_0^2}\delta_{i0}U_{xi} + \sum_p U_{xp}\varepsilon_{i-p} \quad (14)$$

$$\frac{\partial U_{xi}}{\partial z'} = \left[\frac{k_y^2}{k_0^2}(1-\delta_{i0}) + \frac{k_{xi}^2}{k_0^2}\right]S_{yi} - \sum_p S_{yp}\varepsilon_{i-p}$$

where $z'=k_0 z$ and $\delta_{ij}=1$ for $i=j$ and $\delta_{ij}=0$ for $i\neq j$. In matrix form, Eq. 14 gives $$\left[\frac{\partial S_y}{\partial z'}\right] = [I - n_1^2\sin^2\theta\delta_{i0}E^{-1}] \cdot U_x \quad (15)$$

$$\left[\frac{\partial U_x}{\partial z'}\right] = [K_x^2 - E + n_1^2\sin^2\theta(I-\delta_{i0})] \cdot S_y.$$

The eigenvalue equation of Eq. 15 can be further simplified to a second derivative equation $$\left[\frac{\partial^2 S_y}{\partial z'^2}\right] = [B \cdot A] \cdot S_y \quad (16)$$

where $$B = I - [n_I^2 \sin^2\theta\delta_{i0}]E^{-1},$$

$$A = K_x^2 + [n_I^2 \sin^2\theta(I-\delta_{i0})] - E. \quad (17)$$

In the preceding equations, matrices $I$, $K_x$ and $E$ are as defined in Eq. A10.

As for the normal incident plane case ($\phi=0$) (e.g., as in Appendix A2), the main space harmonic component of the field $S_{yi}$, $U_{xi}$ in the grating region is expressed as $$S_{yi}(z) = \sum_{m=1}^n w_{i,m}\{c_m^+\exp(-k_0 q_m z) + c_m^-\exp[k_0 q_m(z-d)]\} \quad (18)$$

$$U_{xi}(z) = \sum_{m=1}^n v_{i,m}\{-c_m^+\exp(-k_0 q_m z) + c_m^-\exp[k_0 q_m(z-d)]\}$$

$v_{i,m}$ are the elements of matrix $V=WQ$, and $Q$ is a diagonal matrix with elements $q_m$. Here the matrix $A$ of Eq. 16 has eigenvalues $q_m$ and corresponding eigenvectors $w_{i,m}$, which are the columns of the matrix $W$.

The boundary condition at $z=0$ (i.e., continuity of tangential field components) leads to $$R_{si} = \cos\varphi_i \cdot S_{yi}(0) - \sin\varphi_i \cdot S_{xi}(0) - \quad (19)$$

$$j\frac{k_{1,zi}}{k_0}R_{si} = -\cos\varphi_i \cdot U_{xi}(0) - \sin\varphi_i \cdot U_{yi}(0)\cos\theta -$$

$$j\frac{k_{1,zi}}{k_0 n_1^2}R_{pi} = \cos\varphi_i \cdot S_{xi}(0) + \sin\varphi_i \cdot S_{yi}(0) -$$

$$jn_1 + R_{pi} = -\cos\varphi_i \cdot U_{yi}(0) + \sin\varphi_i \cdot U_{xi}(0)$$

For this case, the electric field of the incident wave and zero order diffracted waves is in the Y-Z plane (of FIGS. 1, 2a and 2b), which corresponds to p-polarization. According to the assumption above, the electric field of other diffraction orders is perpendicular to the diffraction plane that corresponds to s-polarization. So in Eqs. 19, we set $R_{s0}=0$, and $R_{pi}=0$ ($i\neq 0$).

Typically, characterization is based on measurement of the zero order reflection into region I. From Eqs. A16 and A20, the reflection coefficients are given by $$R_i = \begin{cases} -jR_{p0}/n_1, & i=0 \\ R_{si}, & i\neq 0 \end{cases}. \quad (20)$$

Using Eqs. 13, 18, and 20, Eqs. 19 can be put into a matrix form given by $$\begin{bmatrix}\cos\theta\cdot\delta_{i0}\\ jn_1\delta_{i0}\end{bmatrix} + \begin{bmatrix}Y_c\\ -jY_1\end{bmatrix}R = \begin{bmatrix}W & WX\\ V & -VX\end{bmatrix}\begin{bmatrix}C^+\\ C^-\end{bmatrix}, \quad (21)$$

where $Y_c$, $Y_1$ are diagonal matrices with i,i elements given by $\cos\theta\cdot\delta_{i0}+\cos\phi_i(1-\delta_{i0})$ and $n_I\delta_{i0}-(k_{I,zi}/k_0)\cos\phi_i(1-\delta_{i0})$, respectively. Here $X$ is a diagonal matrix with elements $\exp(-k_0 q_m d)$.

At $z=d$, taking account of Eq. 13, continuity of the tangential field components leads to $$S_{yi}(d) = \sum_{m=1}^n w_{i,m}[c_m^+\exp(-k_0 q_m d) + c_m^-] = T_{si}\cos\varphi_i, - \quad (22)$$

$$U_{xi}(d) = \sum_{m=1}^n V_{i,m}[c_m^+\exp(-k_0 q_m d) - c_m^-] = j\frac{k_{11,zi}}{k_0}\cos\varphi_i \cdot T_{si},$$

$$U_{x0}(d) = \sum_{m=1}^n v_{0,m}[-c_m^+\exp(-k_0 q_m d) + c_m^-] = T_{p0},$$

$$S_{y0}(d) =$$

$$\sum_{m=1}^n w_{0,m}[c_m^+\exp(-k_0 q_m d) + c_m^-] = \frac{j}{n_{11}^2}(n_{11}^2 - n_1^2\sin^2\theta)^{1/2}T_{p0}.$$

Let:

$$T_i = \begin{cases} jT_{p0}/n_{11}, & i=0 \\ T_{si}, & i\neq 0 \end{cases}. \quad (23)$$

Eqs. 22 and 23 give $$\begin{bmatrix}WX & W\\ VX & -V\end{bmatrix}\begin{bmatrix}C^+\\ C^-\end{bmatrix} = \begin{bmatrix}Z_c\\ jY_2\end{bmatrix}T \quad (24)$$

where $Z_c$, $Y_2$ are diagonal matrices with i,i elements $(1-n_I^2\sin^2\theta/n_{II}^2)^{1/2}\delta_{i0}+\cos\phi_i$ and $n_{II}\delta_{i0}-k_{II,zi}\cos\phi_i/k_0$, respectively.

Then, the reflection coefficients $R_i$ can be obtained by solving the eigenvalue problem of Eqs. 16 and then solving the boundary conditions given by Eqs. 21 and 24 simultaneously.

1c) TM Mode ($\phi=\pi/2$, Small $\theta$)

As for the TE mode case, the field components in the grating region are obtained from the second of Eqs. A7

$$k_0^2 E_{gx} = \frac{\partial^2 E_{gy}}{\partial x \partial y} - \frac{\partial^2 E_{gx}}{\partial y^2} + j\omega\mu_0 \frac{\partial H_{gy}}{\partial z}. \tag{25}$$

From Eq. (7), we have $$k_0^2 \sum_i \sum_h \varepsilon_h S_{xi} \exp[-jk_{x,i+h}x] = - \tag{26}$$
$$k_y \sum_i k_{xi} S_{yi} \exp(-jk_{xi}x) + k_y^2 \sum_i S_{xi} \exp(-k_{xi}x) +$$
$$k_0 \sum_i \frac{\partial U_{yi}}{\partial z} \sum_h \varepsilon_h \exp(-jk_{xi}x)$$

Following similar steps as in the TE mode development, we have $$k_0^2 \sum_p S_{xp} \varepsilon_{i-p} = -k_y k_{xi} S_{yi} + k_y^2 U_{xi} + k_0 \frac{\partial U_{yi}}{\partial z}. \tag{27}$$

From the first of Eqs. A7, we have $$k_0^2 H_{gy} = j\left(\frac{\varepsilon_0}{\mu_0}\right) \frac{\partial E_{gx}}{\partial z} - \frac{\partial}{\partial x}\left[\frac{1}{\varepsilon(x)}\left(\frac{\partial H_{gy}}{\partial x} - \frac{\partial H_{gx}}{\partial y}\right)\right]. \tag{28}$$

Now, the inverse relative permittivity $1/\epsilon(x)$ is expressed as a Fourier series having coefficients $a_h$ shown in Eqs. A22 and A23. Substituting these coefficients into Eqs. 7 and A8, we have $$-j\sum_i U_{yi} \exp(-jk_{xi}x) = \frac{j}{k_0} \sum_i \frac{\partial S_{xi}}{\partial z} \exp(-jk_{xi}x) + \tag{29}$$
$$\frac{1}{k_0^2} \frac{\partial}{\partial x}\left[\sum_i (k_{xi} U_{yi} - k_y U_{xi}) \sum_h a_h \exp(-jk_{x,i+h}x)\right].$$

With similar steps applied to the first of Eqs. A7, we have $$\frac{\partial S_{xi}}{\partial z'} = \frac{1}{k_0^2} \sum_p k_{xi} a_{i-p}(k_{xp} U_{yp} - k_y U_{xp}) - U_{yi} \tag{30}$$

For TM mode at a near-normal incident angle, $S_{xi}$ and $U_{yi}$ are the main components of the incident field. We assume that the ith order of electric field is within the plane defined by the k vector of the ith order diffraction wave and its projection into the x-y plane, and the same order magnetic field is perpendicular to the k vector and electric field. In this case, $U_{xi}$ and $U_{yi}$ have opposite phases, while $S_{xi}$ and $S_{yi}$ have the same phase. The purpose of this assumption is to simplify the calculation by neglecting polarization coupling, and the error of the approximation is small for small incident angles. A similar assumption is made above for the small angle TE case.

Thus we have $$\frac{S_{yi}}{S_{xi}} = -\frac{U_{xi}}{U_{yi}} = \begin{Bmatrix} 0, & i=0 \\ \tan\varphi_i, & i\neq 0 \end{Bmatrix} == \mathrm{Tan}\varphi_i \tag{31}$$

With this assumption, Eqs. 27 and 30 give $$\frac{\partial U_{yi}}{\partial z'} = \sum_p S_{xp} \varepsilon_{i-p} - n_1^2 \sin^2\theta \cdot \delta_{i0} S_{x0} \tag{32}$$
$$\frac{\partial S_{xi}}{\partial z'} = \frac{1}{k_0^2} \sum_p \left[k_{xi} a_{i-p} \frac{k_{xp}^2 + k_y^2}{k_{xp}} (1-\delta_{p0}) U_{yp}\right] - U_{yi}$$

Eqs. 32 in second order matrix form give $$\left[\frac{\partial^2 U_y}{\partial z'^2}\right] = [B_M \cdot A_M] \cdot U_y \tag{33}$$

where $$B_M = E - [n_I^2 \sin^2\theta \cdot \delta_{i0} \cdot I]$$
$$A_M = K_x E^{-1} K_{xy} - I \tag{34}$$

and $K_{xy}$ is a diagonal matrix with i,i elements $(k_{xi}/k_0 + k_y^2/(k_0 k_{xi}))(1-\delta_{i0})$.

Now, let $$U_{yi}(z) = \sum_{m=1}^n w_{i,m}\{c_m^+ \exp(-k_0 q_m z) + c_m^- \exp[k_0 q_m(z-d)]\} \tag{35}$$
$$S_{xi}(z) = \sum_{m=1}^n v_{i,m}\{-c_m^+ \exp(-k_0 q_m z) + c_m^- \exp[k_0 q_m(z-d)]\}$$

where $V = B_M^{-1} \cdot W \cdot Q$. Here the matrix $A_M$ of Eq. 34 has eigenvalues $q_m$ and corresponding eigenvectors $w_{i,m}$, which are the columns of the matrix W. The magnetic field of the incident and zero order diffracted waves is in the y-z plane (of FIGS. 1 and 2a-b), which corresponds to s-polarization.

The z=0 boundary conditions give $$\delta_{i0} + R_{si} = \cos\varphi_i \cdot S_{yi}(0) - \sin\varphi_i \cdot S_{xi}(0) = -S_{x0}(0), R_{pi} = \tag{36}$$
$$\sin\varphi_i \cdot U_{xi}(0) - \cos\varphi_i \cdot U_{yi}(0) = -U_{yi}(0)/\cos\varphi_i, -$$
$$j\frac{k_{1,zi}}{k_0 n_1^2} R_{pi} = \cos\varphi_i \cdot S_{xi}(0) + \sin\varphi_i \cdot S_{yi}(0) = S_{xi}(0)/\cos\varphi_i,$$
$$j\left(n_1 \cos\theta \cdot \delta_{i0} - \frac{k_{1,zi}}{k_0} R_{si}\right) = -\cos\varphi_i \cdot U_{yi}(0) - \sin\varphi_i \cdot U_{xi}(0) =$$
$$-U_{y0}(0).$$

According to our assumption the magnetic field of other orders is perpendicular to the diffraction plane that corresponds to p-polarization. So in Eqs. 36, we set $R_{p0}=0$, and $R_{si}=0$ ($i \neq 0$). In this case the reflection coefficients are $$R_i = \begin{cases} -R_{sO}, & i=0 \\ -jR_{pi}/n_1, & i \neq 0 \end{cases}. \tag{37}$$

From Eqs. 35, we have $$1 - R_0 = \sum_{m=1}^{n} v_{0,m}[c_m^+ - c_m^- \exp(-k_0 q_m d)], - \tag{38}$$

$$jn_1 R_i \cos\varphi_i = \sum_{m=1}^{n} w_{i,m}[c_m^+ + c_m^- \exp(-k_0 q_m d)],$$

$$\frac{k_{1,zi}}{k_0 n_1} R_i \cos\varphi_i = \sum_{m=1}^{n} v_{i,m}[-c_m^+ + c_m^- \exp(-k_0 q_m d)], -$$

$$jn_1 \cos\theta - jn_1 \cos\theta \cdot R_0 = \sum_{m=1}^{n} w_{0,m}[c_m^+ + c_m^- \exp(-k_0 q_m d)].$$

In matrix form, Eqs. 38 give $$\begin{bmatrix} -jn_1\delta_{i0}\cos\theta \\ \delta_{i0} \end{bmatrix} + \begin{bmatrix} Y_c \\ -jZ_1 \end{bmatrix} R = \begin{bmatrix} W & WX \\ V & -VX \end{bmatrix} \begin{bmatrix} C^+ \\ C^- \end{bmatrix}, \tag{39}$$

where $Y_c$, $Z_1$ are diagonal matrices with i,i elements given by $-jn_i(\cos\theta \cdot \delta_{i0} + \cos\varphi_i)$ and $$-j\left(\delta_{i0} + \frac{k_{1,zi}}{k_0 n_1}\cos\varphi_i 0\right),$$

respectively.

At $z=d$, accounting for Eq. 31, continuity of tangential field components gives $$-S_{xO}(d) = \sum_{m=1}^{n} v_{0,m}[c_m^+ \exp(-k_0 q_m d) - c_m^-] = T_{sO}, \tag{40}$$

$$-U_{yO}(d) = -\sum_{m=1}^{n} w_{0,m}[c_m^+ \exp(-k_0 q_m d) + c_m^-] = j\frac{k_{II,z0}}{k_0} T_{sO},$$

$$U_{yi}(d) = \sum_{m=1}^{n} w_{i,m}[c_m^+ \exp(-k_0 q_m d) + c_m^-] = T_{pi}\cos\varphi_i,$$

$$S_{xi}(d) = \sum_{m=1}^{n} v_{i,m}[-c_m^+ \exp(-k_0 q_m d) + c_m^-] = j\left(\frac{k_{II,zi}}{k_0 n_{II}^2}\right) T_{pi}\cos\varphi.$$

By defining $$T_i = \begin{cases} -T_{sO}, & i=0 \\ -jT_{pi}/n_{II}, & i \neq 0' \end{cases} \tag{41}$$

Eqs. 40 in matrix form give $$\begin{bmatrix} WX & W \\ VX & -V \end{bmatrix} \begin{bmatrix} C^+ \\ C^- \end{bmatrix} = \begin{bmatrix} Z_c \\ jZ_2 \end{bmatrix} T, \tag{42}$$

where $Z_c$, $Z_2$ are diagonal matrices having i,i elements given by $jk_{II,zi}\delta_{i0}/k_0 + jn_{II}\cos\varphi_i$ and $$j\left(\delta_{i0} + \frac{k_{II,zi}}{k_0 n_{II}}\cos\varphi_i\right),$$

respectively.

The reflection coefficients $R_i$ can be obtained by solving the eigenvalue problem of Eqs. 33 and then solving the boundary conditions given by Eqs. 39 and 42 simultaneously.

The small incident angle approximation discussed above in sections 1b and 1c also assumes the incident plane is parallel to the grating lines. Thus the method for reducing matrix dimension given in section 1a is also applicable to the results of these sections. In this way, matrices A and B in Eq. 17 and matrices $A_M$ and $B_M$ in Eq. 34 can be reduced according to Eq. 4. Since multiplication of matrices keeps the same form after reducing dimension (as in Eq. 6), all other matrices developed from A, B in TE mode or from $A_M$, $B_M$ in TM mode will keep the same form during this process.

1d) Multilayer Gratings

For multi-layer gratings, the partial solution approach as outlined in Moharam et al. (JOSA v12 pp. 1077-1086 1995, especially pp. 1084-1085) is applicable to any of the methods described in sections 1a-c, provided the multi-layer grating is symmetric. A symmetric multi-layer grating is a grating where each layer has reflection symmetry about a symmetry plane common to all layers. Note that a single layer binary grating (e.g., as shown on FIG. 1) is always symmetric in this sense. The geometry for multi-layer gratings is a straightforward generalization of the geometry of FIG. 1, where region 112 consists of L layers, each layer being a binary grating as on FIG. 1, or a symmetric non-binary grating. Here layer l occupies the region $d_l - d_{l-1} < z < d_l$, where $d_l$ is the depth of the deeper interface of layer l. In the following description, matrices and vectors carry subscripts indicating the layer to which they relate.

For example, from the boundary conditions of Eqs. 21, 24, 39, and 42, the boundary condition between layer l and l−1 (at $z=d_{l-1}$) will be $$\begin{bmatrix} W_{l-1}X_{l-1} & W_{l-1} \\ V_{l-1}X_{l-1} & -V_{l-1} \end{bmatrix} \begin{bmatrix} C_{l-1}^+ \\ C_{l-1}^- \end{bmatrix} = \begin{bmatrix} W_l & W_l X_l \\ V_l & -V_l X_l \end{bmatrix} \begin{bmatrix} C_l^+ \\ C_l^- \end{bmatrix}. \tag{43}$$

Let: $f_{L+1}=Z_c$, $g_{L+1}=jY_2$, and $C_{L+1}=T$, Eq. 42 can be written as $$\begin{bmatrix} -W_L & f_{L+1} \\ V_L & g_{L+1} \end{bmatrix} \begin{bmatrix} C_L^- \\ C_{L+1}^+ \end{bmatrix} = \begin{bmatrix} W_L X_L \\ V_L X_L \end{bmatrix}[C_L^+]. \tag{44}$$

The above 2n dimensional matrix equation can be divided into two n dimensional matrix equations. Eliminating $C_{L+1}$ with the two equations, we can find:

$$C_L^- = a_L C_L^+, \tag{45}$$

where $$a_L = (V_L + g_{L+1} f_{L+1}^{-1} W_L)^{-1} (V_L - g_{L+1} f_{L+1}^{-1} W_L) X_L. \quad (46)$$

The boundary condition between L and L−1 layer of grating can also be written in the form of Eq. 44. By comparing with Eq. 43, we have $$f_L = W_L(I + X_L a_L)$$

$$g_L = V_L(I - X_L a_L) \quad (47)$$

By repeating the same process, a, f, and g can be found for each layer in succession from layer L−1 to layer 1. At layer 1, we have $$\begin{bmatrix} D \\ DD \end{bmatrix} + \begin{bmatrix} Y_c \\ -jYZ \end{bmatrix} R = \begin{bmatrix} f_1 \\ g_1 \end{bmatrix} [C_1^+], \quad (48)$$

where $$D = \begin{cases} \delta_{i0}\cos\theta, & \text{for } TE \\ -jn_1\delta_{i0}\cos\theta, & \text{for } TM \end{cases}, \quad DD = \begin{cases} jn_1\delta_{i0}, & \text{for } TE \\ \delta_{i0}, & \text{for } TM \end{cases}. \quad (49)$$

and i is the diffraction order. The matrix $YZ = Y_1, Z_1$ for TE, TM mode, respectively. From Eq. 48, the reflections $$R = (Y_c + j \cdot f_1 \cdot g_1^{-1} \cdot YZ)^{-1} \cdot (DD \cdot f_1 \cdot g_1^{-1} - D) \quad (50)$$

can be calculated.

In this approach, only the reflection coefficients of the diffraction are calculated. It simplifies the calculation by about a factor of two by not computing the transmission coefficients. Also, matrix reduction as in section 1a, where every matrix is replaced by its reduced equivalent, is applicable to the results of this section.

2) EXAMPLES

2a) Comparison of Small θ Results to SRCWA

Figure 3A:
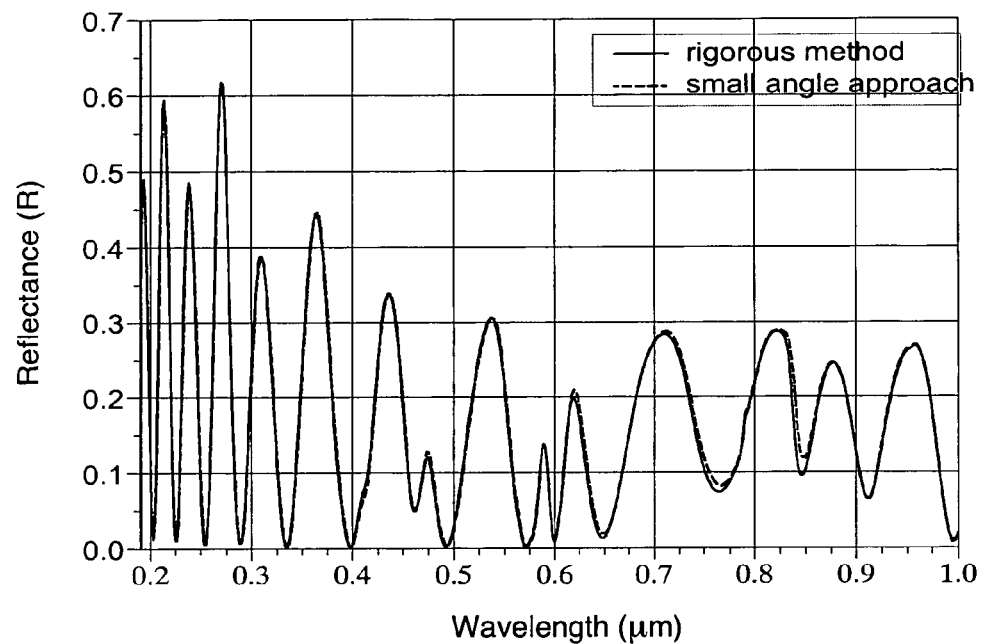
FIGS. 3a and 3b show a TE mode small incidence angle approximation calculation according to an embodiment of the invention.

FIG. 3a shows a comparison of zero order reflectance (i.e., $R = |R_0|^2$) calculated by the SRCWA of section 1a and by the small angle approximation of section 1b (i.e., TE mode). The calculations are performed for a binary silicon/air grating with $\Lambda = 0.8$ μm, $d = 1$ μm and $f = 0.4$ on a silicon substrate. The angle of incidence is 9 degrees, and the two lines are almost overlapping except for small parts of the spectrum.

Figure 3B:
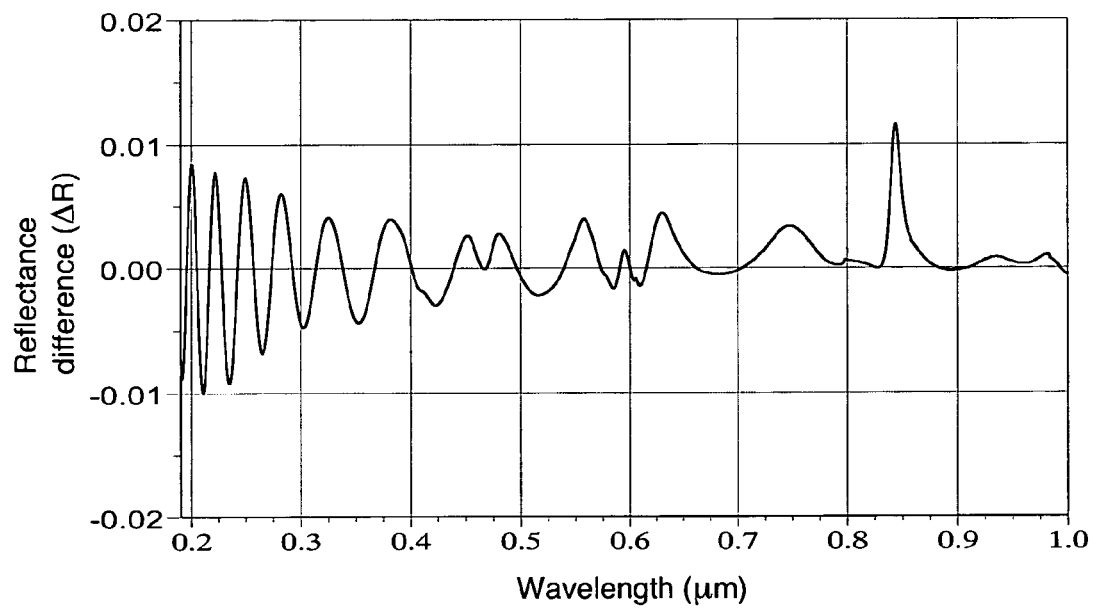

FIG. 3b shows the same calculation for a 4 degree incident angle, where the difference ΔR between rigorous and approximate results for $|R_0|^2$ is plotted. The difference is limited to about ±0.01, which means the maximum approximation error is about 3%, and the average approximation error is about 1%.

Figure 4A:
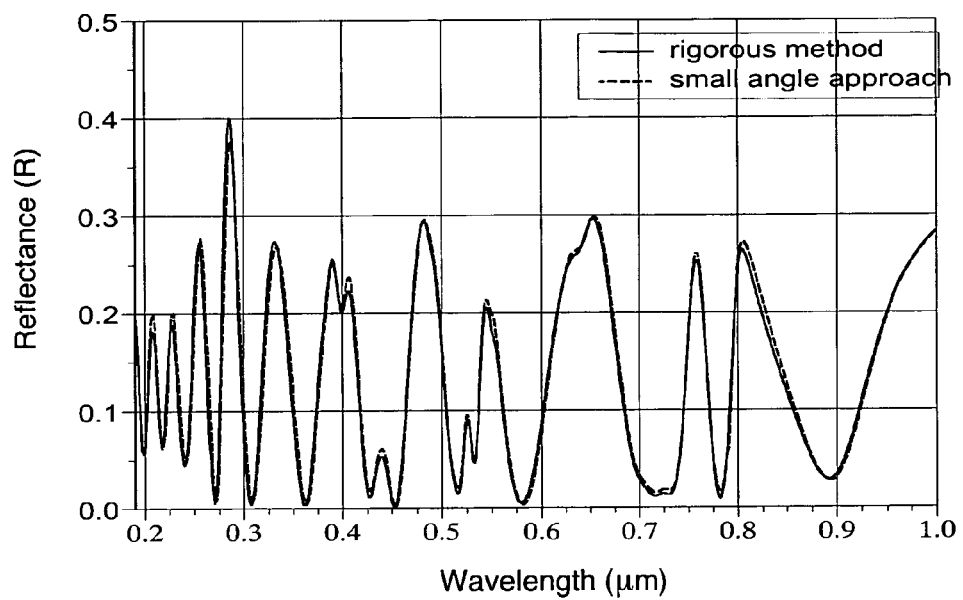
FIGS. 4a and 4b show a TM mode small incidence angle approximation calculation according to an embodiment of the invention.
Figure 4B:
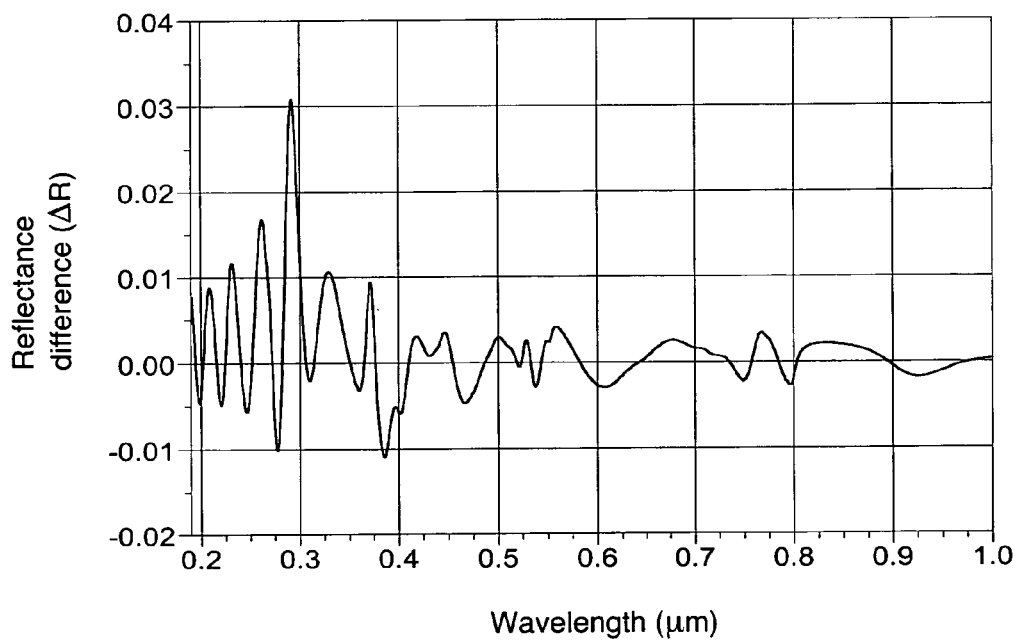

FIGS. 4a and 4b correspond to FIGS. 3a and 3b, except that the results of FIGS. 4a-b relate to the TM mode (i.e., the results of section 1c are used for the approximate results). The results are similar to those of FIGS. 3a-b, except that the error is slightly higher (i.e., maximum error about 7~8% and average error about 1~2% on FIG. 4b).

2b) Normal Incident Angle Approximation (Revised Grating d)

As shown in sections 1b-c, the small angle approach provides a good approximation for simulation of the grating reflection. However, for conical diffraction with a small angle of incidence, an alternate approximation method can also be used, where normal incident angle is assumed in the calculations to simplify them. This normal incident angle approximation includes three alternatives. In the first alternative, normal incident angle calculations as in part 2 of Appendix A are performed. If the incident angle is sufficiently small, the error incurred is negligible. The second alternative includes a modification to the grating depth to improve accuracy. The third alternative includes a modification to the grating index to improve accuracy. Sections 2b and 2c relate to modification of grating depth and grating index respectively (i.e., the second and third alternatives for the normal incident angle approximation).

Figure 5A:
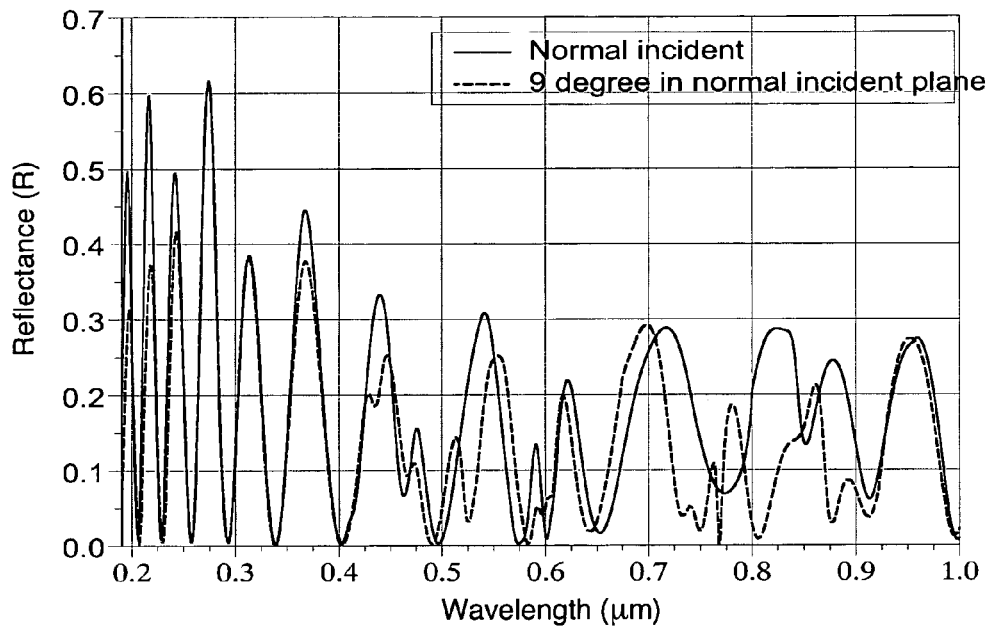
FIGS. 5a and 5b show the TE mode reflection spectra from a normal angle incident beam ($\theta$=0, solid line) and from a small angle incident beam with the incident plane normal to the grating lines (dashed lines).
Figure 5B:
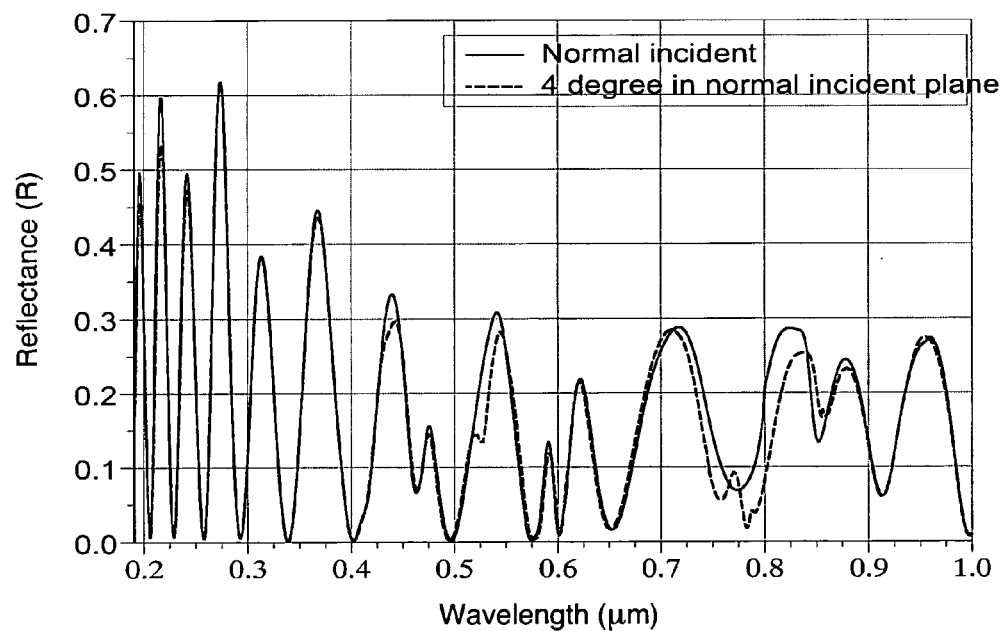

This normal incident angle approximation is especially suitable for symmetric conical diffraction (i.e., $\phi = \pi/2$), where the plane of incidence is parallel to the grating lines, since for this case, a nonzero (but small) angle of incidence does not eliminate the symmetry of the diffraction problem. In contrast, a nonzero angle of incidence for planar diffraction (i.e., $\phi = 0$) breaks the symmetry of the diffraction problem. Thus the difference between normal incident angle (θ=0) diffraction and off-normal (θ>0) incident angle diffraction will be less for symmetric conical diffraction than for planar diffraction. FIGS. 5a and 5b show zero order reflectance calculations for the example of FIGS. 3a and 3b, by assuming planar diffraction. The solid lines show the reflectance for a normal incident angle, while the dotted lines show the reflectances for 9 degree (FIG. 5a) and 4 degree (FIG. 5b) incident angles. Comparison of FIGS. 5a-b with FIGS. 6a-b, 7a-b and 8a-b shows a much larger difference between normal incident angle and off-normal incident angle for planar diffraction (i.e., FIGS. 5a-b) than for symmetric conical diffraction (i.e., FIGS. 6a-b, 7a-b and 8a-b). It is convenient to refer to symmetric conical diffraction as "parallel incidence" in the following description.

For normal incident angle (θ=0) calculations, the eigenvalue equation and boundary conditions are given by Eqs. A21, A25 and A26 with θ=0 and reduced matrices as in Eq. A27. For parallel incidence, $k_y$ and $k_{I,zi}$ depend on θ. Since $k_y$ does not affect diffraction, the relevant effect is the dependence of $k_{I,zi}$ on θ. For the zero order:

$$k_{I,z0} = k_0 n_I \cos\theta. \quad (51)$$

For normal incident angle we have $k_{I,z0} = k_0 n_I$ for zero order diffraction.

The modified d (or revised d) normal incident angle approximation is based on replacing d with d·cos θ in an otherwise standard normal incident angle calculation. This approach ensures that the change in phase $k_{I,z0}d$ due to off-normal incident angle is accounted for by altering d. For a simple binary grating (e.g., an air-Si grating), only the line depth needs to be revised in this method, since the trench depth in this case has no independent significance. For symmetric gratings having multiple regions with different indices $n_i$ and the same depth d, Eq. 51 is applicable if cos(θ) is replaced with an average $$\cos\overline{\theta} = \sum_i f_i \cdot \text{real}(n_i) \cdot \cos\theta_i / \sum_i f_i \cdot \text{real}(n_i) \qquad (52)$$

over the grating regions, where $\theta_i$ is defined by $n_i \sin \theta_i = n_I \sin \theta$ and $f_i$ is the filling factor for region i. Thus in this case, d is replaced with $d \cos \overline{\theta}$ throughout an otherwise standard normal incident angle calculation.

Figure 6A:
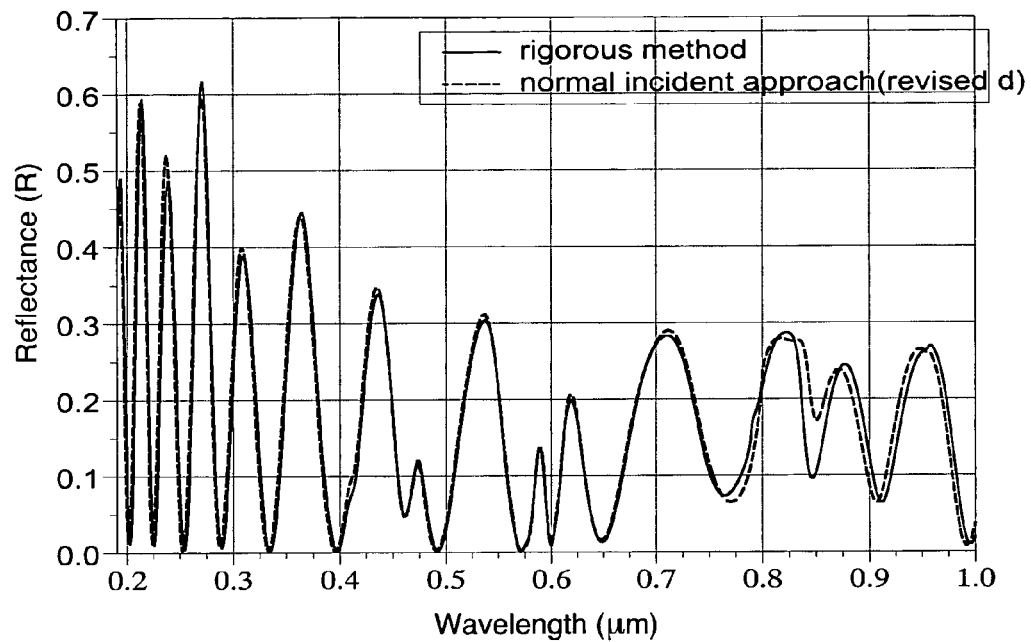
FIGS. 6a and 6b show a TE mode normal incident angle approximation (revised depth) calculation according to an embodiment of the invention.
Figure 6B:
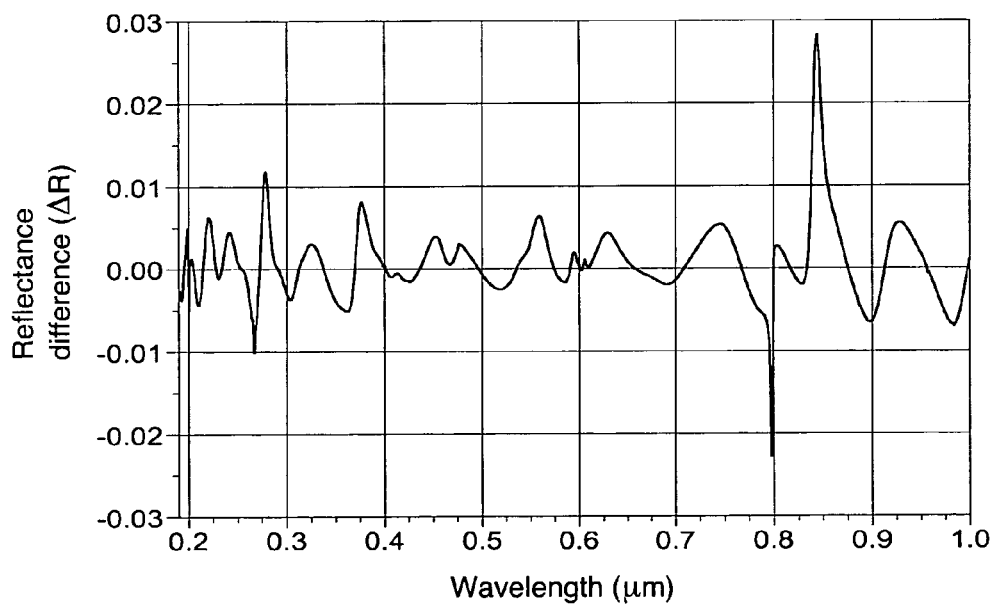
Figure 7A:
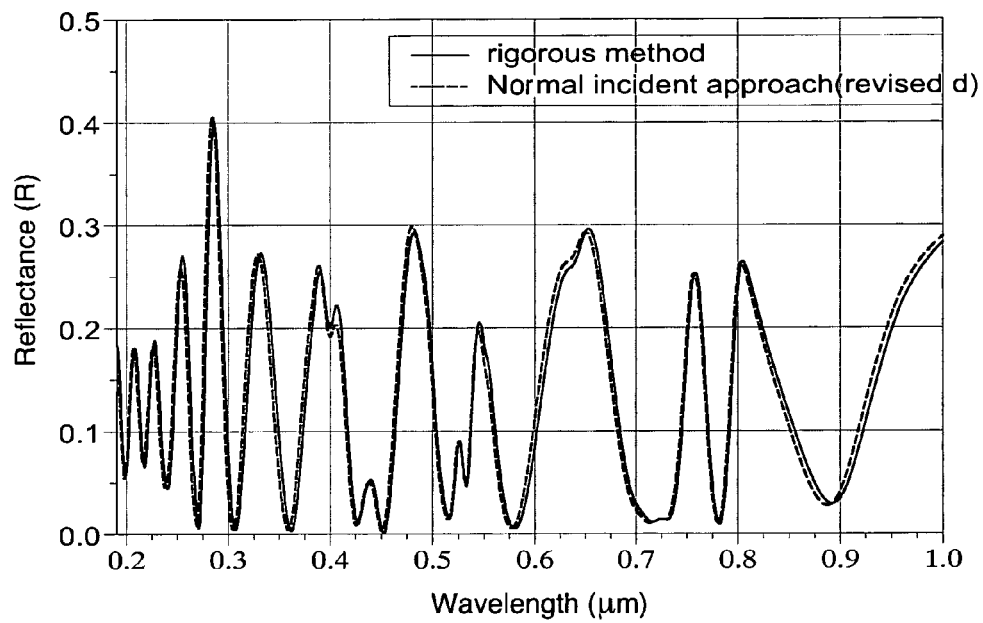
FIGS. 7a and 7b show a TM mode normal incident angle approximation (revised depth) calculation according to an embodiment of the invention.
Figure 7B:
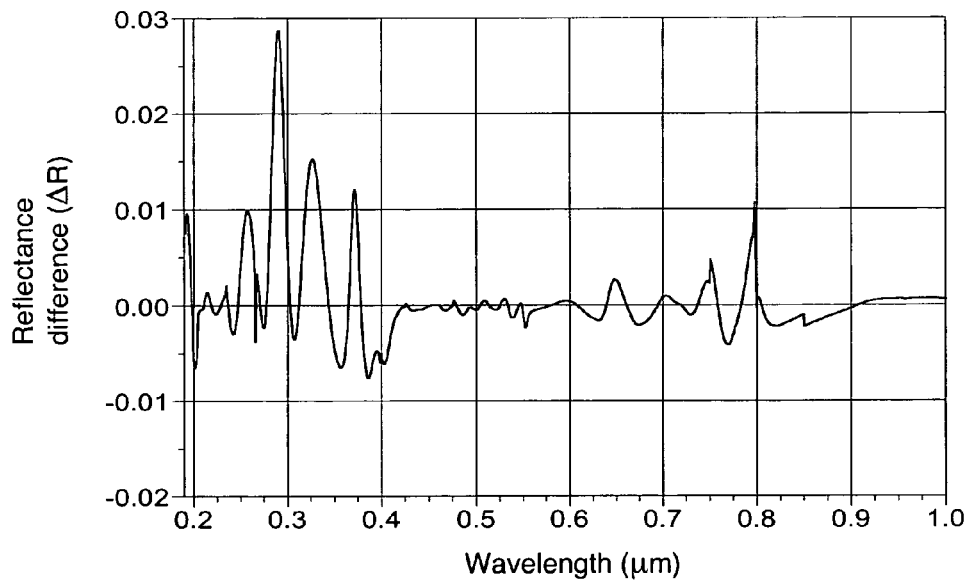

FIGS. 6a-b show the same example as in FIGS. 3a-b (TE mode) where rigorous results are compared to revised d normal incident angle approximation results. Angles of incidence on FIGS. 6a and 6b are 9 degrees and 4 degrees respectively. The grating parameters are as in FIGS. 3a-b. The error in FIGS. 6a-b is a little larger than on FIGS. 3a-b, with a maximum error of about 7~8% and an average error of about 1~2%. FIGS. 7a-b show the same example as in FIGS. 6a-b but for TM mode. Angles of incidence on FIGS. 7a and 7b are 9 degrees and 4 degrees respectively. The grating parameters are as in FIGS. 3a-b. The error is similar to that of FIGS. 4a-b with a maximum error of about 7~8% and an average error of about 1~2%.

2c) Normal Incident Angle Approximation (Revised Index)

Instead of revising the depth of the grating, it is also possible to revise its refractive indices to improve the accuracy of the normal incident angle approximation. The revised index approach is based on setting $n_i$ to $n_i \cos \theta_i$ for all materials (indexed by i) making up the grating structure (included the substrate) throughout an otherwise standard normal incident angle RCWA calculation. Here the angles $\theta_i$ are propagation angles determined by Snell's law:

$$n_i \sin \theta_i = n_I \sin \theta \qquad (53)$$

where incidence from region I is assumed, and $n_I$ is the index of region I. Each refractive index is revised to an "effective index" that provides the proper phase shift in the z-direction. The revised index approach is similar to the revised d approach, except that the $\cos(\theta)$ factors are applied to the indices instead of to the depth. This revised index approximation is applicable to TE mode calculations with the plane of incidence parallel to the grating lines.

For TE mode, once the indicated substitutions are made in Eq. A8, the (reduced matrix) eigenproblem of Eq. A21 is applicable.

Figure 8A:
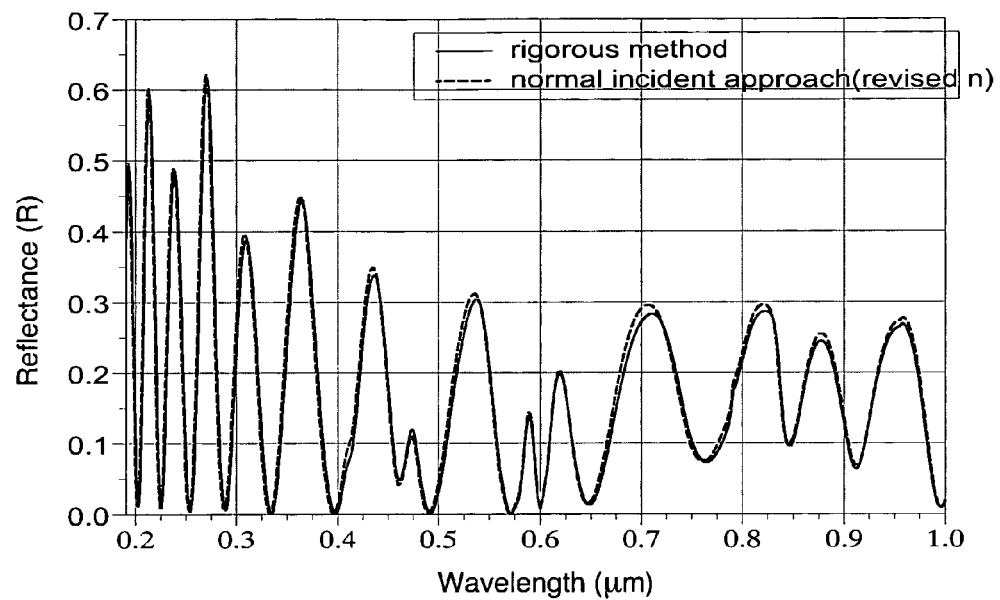
FIGS. 8a and 8b show a TE mode normal incident angle approximation (revised indices) calculation according to an embodiment of the invention.
Figure 8B:
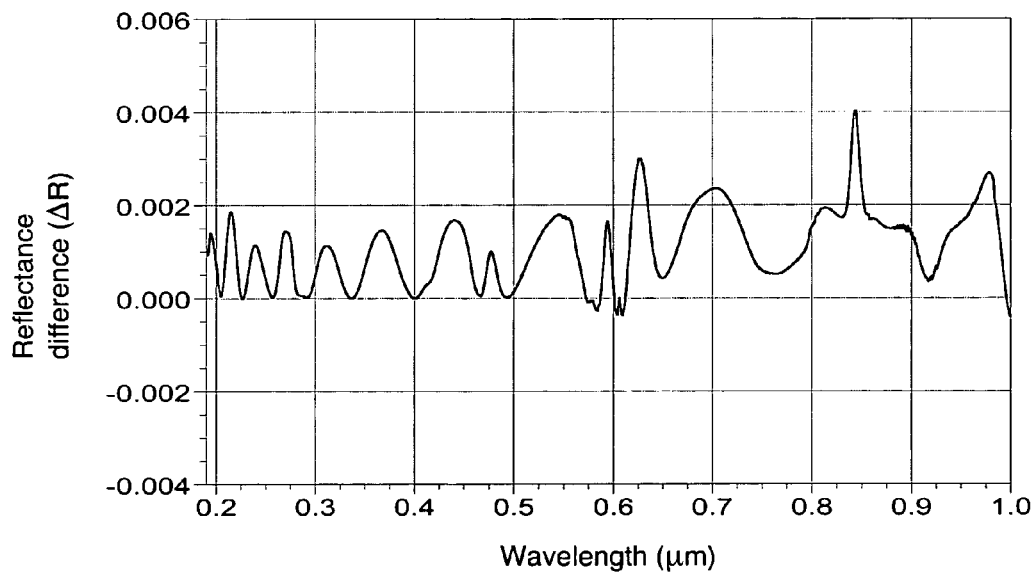

FIGS. 8a-b show the same example as in FIGS. 6a-b, but for normal incident angle approximation with revised refractive indices. Angles of incidence on FIGS. 8a and 8b are 9 degrees and 4 degrees respectively. The grating parameters are as in FIGS. 3a-b. The error is smaller than that of FIGS. 6a-b (revised d) with a maximum error of less than 2% and an average error of about 0.5%. For the 4 degree incident angle, the result of the normal incident angle approach (FIG. 8b) with revised index is even better than that of the small angle approach (FIG. 3b). For the 9 degree incident angle, the normal incident angle approach (FIG. 8a) is not as accurate as the small angle approach (FIG. 3a). The normal incident angle approaches have decreasing accuracy as the incident angle increases, since the effect of the nonzero incident angle is only approximately accounted for. With this approach, the error will tend to decrease as the refractive index contrast of the grating decreases.

The approximations considered in sections 2b and 2c all run at comparable speeds, and provide a significant reduction of calculation time compared to the rigorous approach of section 2a. An example of relative timing results is shown in Table 1 above.

2d) Sensitivity to Changes in Slot Width and Depth

In order to appreciate the significance of the approximation errors in the above-given examples, it is useful to consider the sensitivity of the zeroth order reflectivity to changes in grating linewidth and depth, since these parameters are typically of most interest for characterizing gratings.

Figure 9:
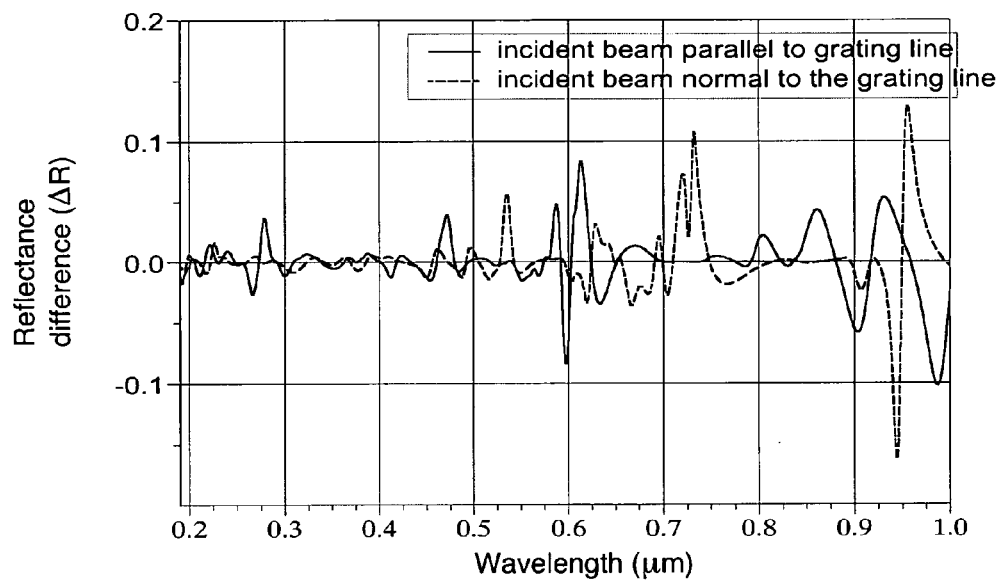
FIG. 9 shows TE mode sensitivity of the zero order reflectance to a change in the grating slot width for symmetric conical diffraction and for planar diffraction.

FIG. 9 shows the reflectance difference $\Delta R$ due to a slot width change $\Delta w=5$ μm, which is less than 1% compared to the slot width $w=0.6$ μm. The solid line is a TE mode parallel incident plane calculation performed with the rigorous SRCWA of section 1a. The dotted line is a TE mode planar diffraction (i.e., plane of incidence perpendicular to the grating lines) calculation performed with a conventional full RCWA. Other parameters are as in FIGS. 3a-b. The sensitivity to a width change $\Delta w$ is similar for the two cases, which shows that the parallel incidence geometry considered here is as sensitive to changes in $\Delta w$ as the more conventional planar diffraction geometry. The maximum $\Delta R$ in the spectrum is larger than 0.1, and the average $\Delta R$ is about 0.03~0.04.

Figure 10:
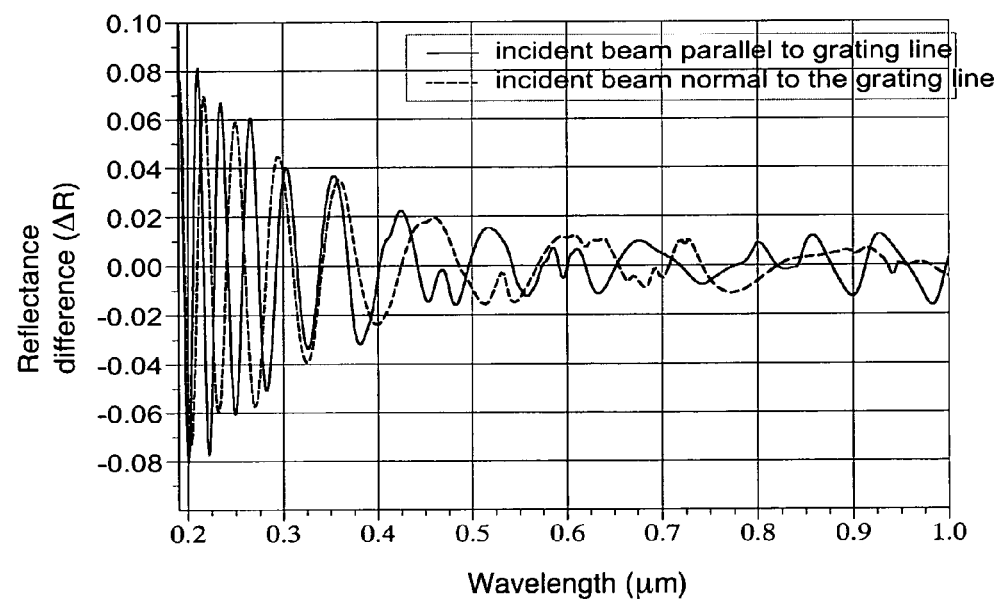
FIG. 10 shows TE mode sensitivity of the zero order reflectance to a change in the grating depth for symmetric conical diffraction and for planar diffraction.

FIG. 10 shows the reflectance difference $\Delta R$ due to a grating depth change $\Delta d=5$ nm, which is 0.5% of the grating depth $d=1$ μm. The solid line is a TE mode parallel incident plane calculation performed with the rigorous SRCWA of section 1a. The dotted line is a TE mode planar diffraction (i.e., plane of incidence perpendicular to the grating lines) calculation performed with a conventional full RCWA. Other grating parameters are as in FIGS. 3a-b. The sensitivity to a depth change $\Delta d$ is similar for the two cases, which shows that the parallel incidence geometry considered here is as sensitive to changes in $\Delta d$ as the more conventional planar diffraction geometry. The maximum $\Delta R$ in the spectrum is about 0.08, and the average $\Delta R$ is about 0.03~0.04.

The differences in the spectrum resulting from a change of less than 1% in slot width and 0.5% in depth of grating are clearly larger than the above-plotted approximation errors in FIGS. 3-8. The above $\Delta d$ and $\Delta w$ are similar to or smaller than typical fabrication errors. So the small angle (TE mode and TM mode) and normal incident angle (revised depth and revised index) approaches both provide useful approximations for grating characterization.

2e) Effect of Beam Divergence

In practice, the incident beam is not an ideal plane wave. Instead, the incident beam includes multiple plane wave components, each of which will have a slightly different zero order reflection from the grating. For example, a beam nominally incident at 4 degrees and having a cone half-angle of 4 degrees will have beam components in the plane of incidence P having incident angles from about 0 degrees to about 8 degrees. A nominal beam component C0 has a wave vector in P at an angle of incidence of 4 degrees. The beam of this example also has a plane wave component C1 having a 5.65 degree angle of incidence in a second plane of incidence P' making an angle of 45 degrees with respect to P. This particular beam component is maximally far from P to emphasize that beam divergence can significantly complicate diffraction calculations by breaking symmetry. Thus if P is parallel to the grating lines, then P' is not, and calculations for the P' beam component are more difficult. With reference to FIG. 1, P lies in a plane of incidence having φ=π/2, and P' lies in a plane of incidence having φ=π/4 (or φ=3π/4).

Figure 11:
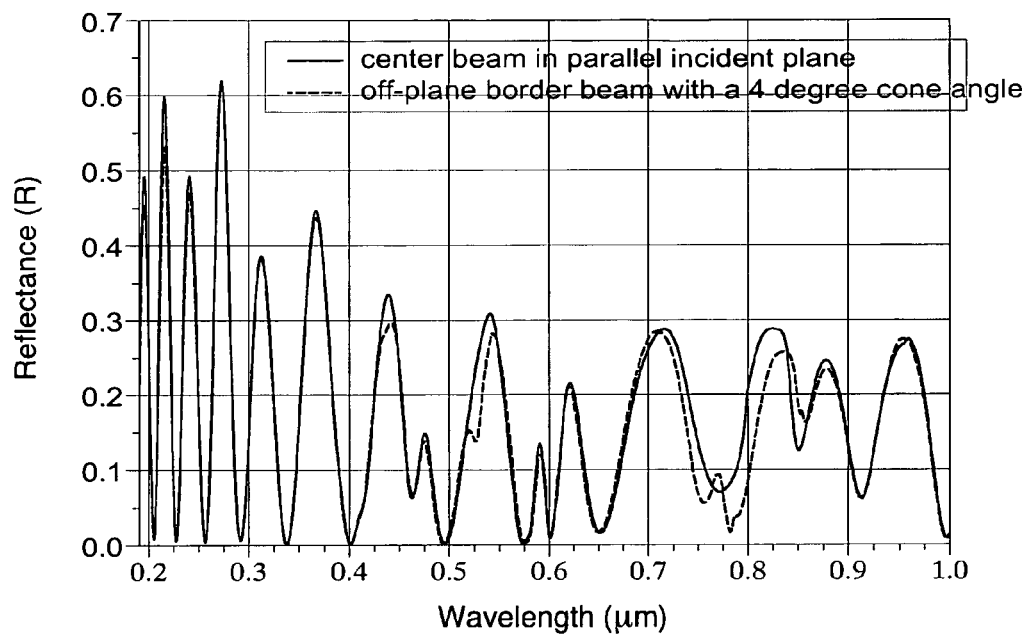
FIG. 11 shows reflectances of on-axis and off-axis beam components.

FIG. 11 shows an example where zero order reflectances are calculated for plane waves C0 (solid line) and C1 (dotted line) using a standard (unsymmetric) RCWA. The grating parameters are as in FIGS. 3a-b. There are noticeable differences between the two curves. To obtain the beam reflectance, an appropriately weighted average of the plane wave reflectances can be calculated. However, it is time consuming to calculate reflectances for plane wave components like C1 that are not in the plane of symmetry.

A suitable approximation for this case is to employ a planar diffraction calculation (since symmetry between positive and negative diffraction orders is broken), where parameters (such as depth or indices) of the planar diffraction calculation are modified as described above in sections 2b and 2c. In the above example, the calculation for beam component C1 would be a planar diffraction calculation for a 4 degree incident angle (since the incident k vector projected into this plane of incidence has a 4 degree angle of incidence). In this planar diffraction calculation, the depth (or indices) would be modified according to a 4 degree tilt angle (since the incident k vector makes an angle of 4 degrees relative to the assumed plane of incidence for planar diffraction).

Figure 12:
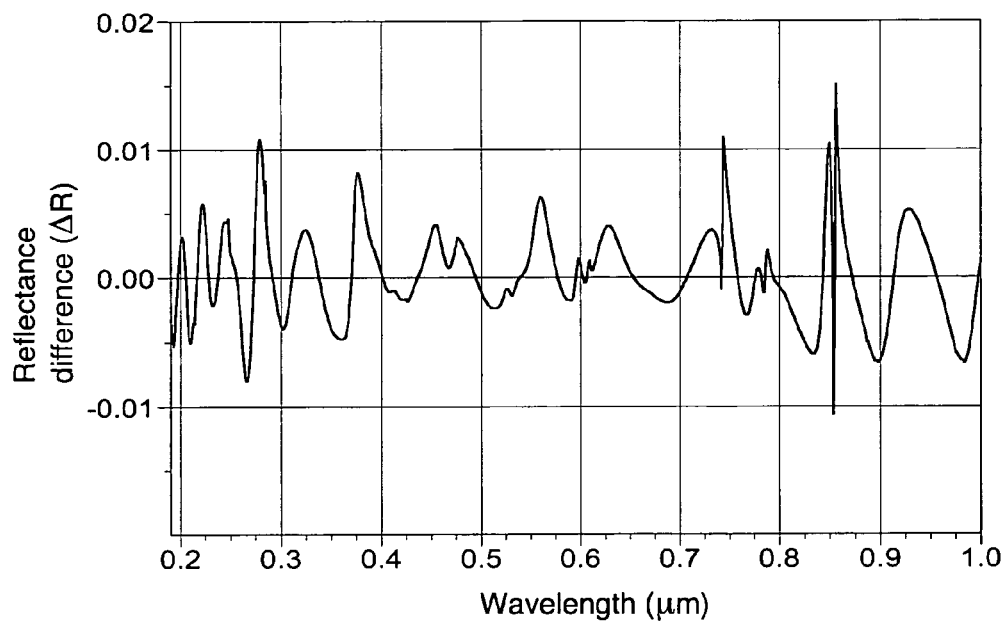
FIG. 12 shows the difference between a rigorous off-axis reflectance calculation and an approximate off-axis calculation based on a planar diffraction calculation.

FIG. 12 shows the difference of the reflectance of plane wave C1 calculated by a standard unsymmetric RCWA and by the above approximation (with revised d). The grating parameters are as in FIGS. 3a-b. The largest error is about 0.015 and the average error is less than 0.01. This is a good approximation, but it requires 2N+1 dimensional matrices instead of N+1 dimensional matrices (since an unsymmetric planar diffraction problem is being solved). In practice, beam divergence can be neglected during most of the curve fitting process, and the above approximation can be optionally included as a refinement during late stages of the curve fit.

2f) Exemplary System

Figure 13:
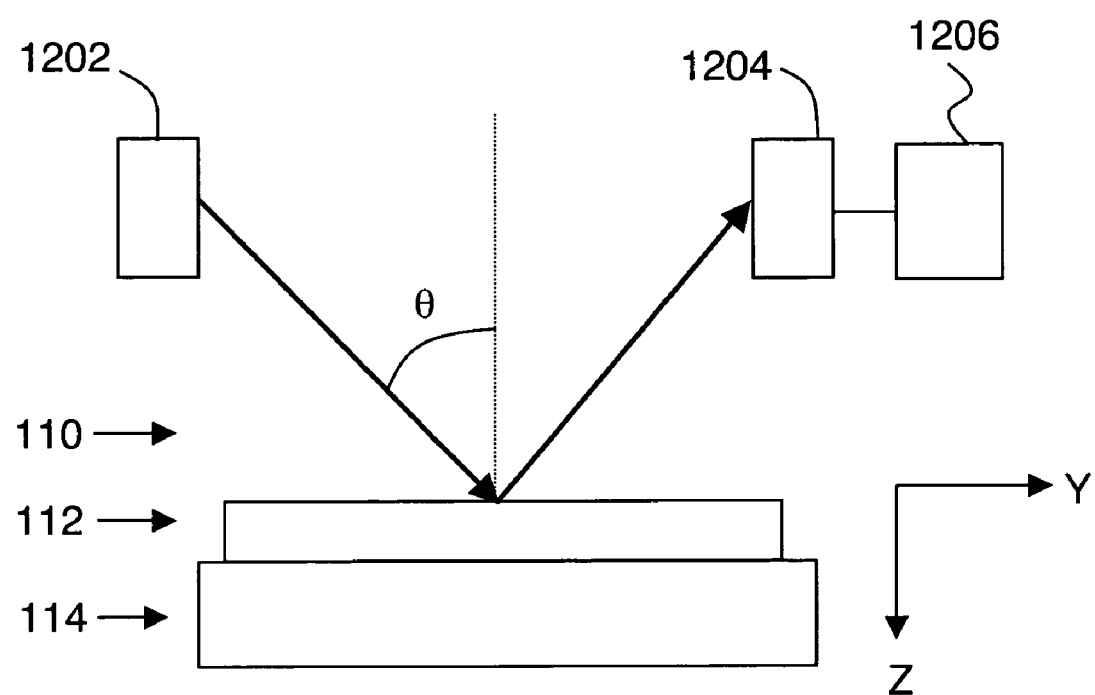
FIG. 13 shows a characterization system according to an embodiment of the invention.
Figure 14:
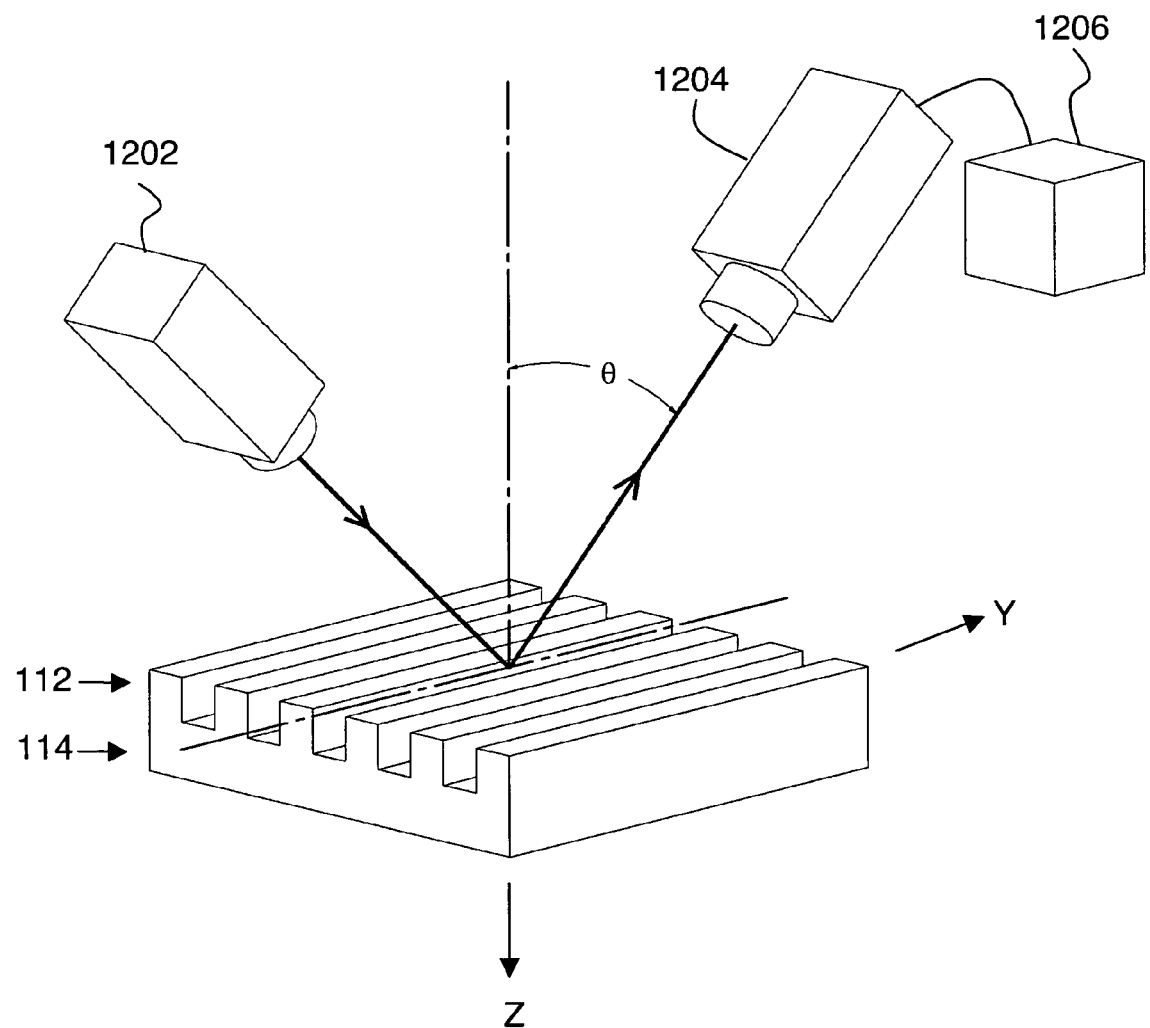
FIG. 14 shows a perspective view of the characterization system of FIG. 13.

FIG. 13 shows a system suitable for practicing various embodiments of the invention. FIG. 14 shows a perspective view of the system of FIG. 13. A sample having a grating 112 separating region I (110) from region II (114) is illuminated by an optical beam from an optical source 1202. A detector 1204 receives a response from the sample. Preferably, this response is the zeroth order reflectance (as shown), but other responses such as transmittances or reflectances into any order can also be detected. The plane of incidence on FIG. 13 is the Y-Z plane, as shown, and the lines of grating 112 are parallel to the Y axis. Thus the illumination geometry of FIG. 13 is symmetric conical diffraction (or parallel incidence). Grating 112 can be a single-layer binary grating (as shown in FIG. 1), or it can be a symmetric multi-layer grating as considered in section 1d.

Detector 1204 is connected to a processor 1206. Processor 1206 preferably controls the wavelength of source 1202 such that a spectral response is measured by detector 1204 and provided to processor 1206. The main function of processor 1206 is to estimate parameters of grating 112 by fitting a modeled response to the measured response provided by detector 1204. The modeled response can be calculated by any of the methods discussed in detail above.

More specifically, the modeled response can be calculated with a symmetric RCWA (section 1a), a small incident angle approximation (sections 1b or 1c), a normal incident angle approximation (sections 2b or 2c), or a beam divergence approximation (section 2e). These methods can be practiced together, unless they are explicitly inconsistent.

Generally, the invention is applicable to symmetric gratings. More specifically, a symmetric grating has even symmetry about a reflection plane parallel to the grating lines. A single-layer binary grating is necessarily symmetric in this sense. Symmetric gratings can also be single-layer non-binary gratings, or multi-layer gratings where each layer is binary or non-binary.

Although the above examples relate to various symmetry-simplified versions of the RCWA, such symmetry simplification according to the invention is also applicable to other analysis methods. For example, the coupled wave method (CWM) with conical incident angle, as described by Lifeng Li in Journal of Modern Optics, V. 40, n.4, p 553-573, 1993, can also be simplified for the case of a symmetric grating and a plane of incidence parallel to the grating lines. In this case, symmetric diffraction from the grating allows a reduction of matrix dimension from 2N+1 to N+1 (for N positive and N negative diffraction orders).

APPENDIX A1

RCWA for Parallel Incident Plane (φ=π/2)

Appendix A provides mathematical results which support the developments given above. More specifically, part 1 of Appendix A provides RCWA results specialized to the case φ=π/2 (i.e., for symmetric conical diffraction or parallel incident plane), and part 2 provides RCWA results specialized to the case φ=0 (i.e., for planar diffraction or normal incident plane). The geometry and notation of Appendix A is consistent with the above description, especially FIG. 1. These results can be regarded as a corrected and slightly modified version of results given by Moharam et al (JOSA, V.12, 1068, 1995).

We assume φ=π/2 in FIG. 1, and expand the electric field in regions I and II as $$E_I = E_{inc} + \sum_i R_i \exp[-j(k_{xi}x + k_y y - k_{1,zi}z)], \quad (A1)$$

$$E_{II} = \sum_i T_i \exp\{-j[k_{xi}x + k_y y + k_{II,zi}(z-d)]\}.$$

Here $$k_{xi} = -i2\pi/\Lambda$$

$$k_y = k_0 n_I \sin\theta \quad (A2)$$

and $$k_{l,zi} = \begin{cases} +[(k_0 n_l)^2 - k_{xi}^2 - k_y^2]^{1/2} & (k_{xi}^2 + k_y^2)^{1/2} < k_0 n_l \\ -j[k_{xi}^2 + k_y^2 - (k_0 n_l)^2]^{1/2} & (k_{xi}^2 + k_y^2)^{1/2} > k_0 n_l \end{cases}, l = I, II. \quad (A3)$$

Generally, ψ is the angle between the electric field E and the incident plane, but it can be beneficial to consider TE and TM modes separately as follows:

$$E_{inc} = (\hat{y}\cos\theta - \hat{z}\sin\theta)\exp[-jk_0 n_I(y\sin\theta + z\cos\theta)], \quad (A4a)$$

for TE mode and $$E_{inc}=-\hat{x}\exp[-jk_0n_I(y\sin\theta+z\cos\theta)], \quad (A4b)$$

for TM mode. This definition of TE and TM modes is made with respect to the grating lines, as discussed above. Here θ is the incident angle within the incident plane, and $R_i$, $T_i$ are normalized vector electric-field amplitudes of reflected waves in region I and transmitted waves in region II respectively.

In the above equations, $n_I$, $n_{II}$ are refractive indices of regions I and II respectively, and $k_0=2\pi/\lambda_0$ where $\lambda_0$ is the wavelength of the incident light in free space. The output angle of the ith order diffraction wave (in the x-y plane) is given by $$\phi_i=\tan^{-1}(k_y/k_{xi}) \quad (A5)$$

The electric and magnetic fields in the grating region (0<z<d) are given by $$E_g = \sum_i [S_{xi}(z)\hat{x} + S_{yi}(z)\hat{y} + S_{zi}(z)\hat{z}]\exp[-j(k_{xi}x + k_y y)], \quad (A6)$$

$$H_g = -j\left(\frac{\varepsilon_0}{\mu_0}\right)^{1/2}\sum_i [U_{xi}(z)\hat{x} + U_{yi}(z)\hat{y} + U_{zi}(z)\hat{z}]\times\exp[-j(k_{xi}x + k_y y)],$$

where $S_i(z)$ $U_i(z)$ are the normalized amplitudes of the ith space-harmonic electric and magnetic fields in the grating. The z components in the above equation are not independent and can be expressed in terms of transverse field components via the equations $$\nabla\times E_g=-j\omega\mu_0 H_g$$

$$\nabla\times H_g=j\omega\varepsilon_0\varepsilon(x)E_g, \quad (A7)$$

Since the grating has a periodic relative permittivity, the permittivity can be expanded in a Fourier series $$\varepsilon(x) = \sum_h \varepsilon_h\exp\left(j\frac{2\pi h}{\Lambda}\right), \quad (A8)$$

where $\varepsilon_h$ is the hth Fourier component of the relative permittivity in the grating region. In the case of a binary grating having ridges and grooves, with indices $n_{rd}$ and $n_{gr}$ respectively, these Fourier components are given by $$\varepsilon_0 = n_{rd}^2 f + n_{gr}^2(1-f) \quad (A9)$$

$$\varepsilon_h = (n_{rd}^2 - n_{gr}^2)\frac{\sin(\pi h f)}{\pi h}$$

where f is the filling factor as shown in FIG. 1. More generally, for a grating having multiple regions indexed by i, the filling factor $f_i$ is the fraction of each region i in the grating. The Fourier components of such a grating are functions of the filling factors $f_i$. The Maxwell equations of Eq. A7 can be expressed as the following matrix eigenvalue equation:

$$\begin{bmatrix} \partial S_y/\partial(z') \\ \partial S_x/\partial(z') \\ \partial U_y/\partial(z') \\ \partial U_x/\partial(z') \end{bmatrix} = \quad (A10)$$

$$\begin{bmatrix} 0 & 0 & K_y E^{-1} K_x & I - K_y E^{-1} K_y \\ 0 & 0 & K_x E^{-1} K_x - I & -K_x E^{-1} K_y \\ K_x K_y & E - K_y^2 & 0 & 0 \\ K_x^2 - E & -K_x K_y & 0 & 0 \end{bmatrix}\begin{bmatrix} S_y \\ S_x \\ U_y \\ U_x \end{bmatrix},$$

where $z'=k_0 z$; E is the matrix formed by the permittivity harmonic components with the i,p element being equal to $\varepsilon_{i-p}$; $K_x$ is a diagonal matrix with the i,i element being equal to $k_{xi}/k_0$; $K_y$ is a diagonal matrix equal to $(k_y/k_0)I$, and I is the identity matrix.

This 4n dimension matrix equation (where n is the number of space harmonics retained in the approximation) can be re-written as two n dimensional matrix equations as follows:

$$[\partial^2 U_x/\partial(z')^2] = [k_y^2 I + A][U_x],$$

$$[\partial^2 S_x/\partial(z')^2] = [k_y^2 I + BE][S_x], \quad (A11)$$

where $$A = K_x^2 - E,$$

$$B = K_x E^{-1} K_x - I. \quad (A12)$$

The space harmonics of the tangential magnetic and electric fields are given by:

$$U_{xi}(z) = \sum_{m=1}^n w_{1,i,m}\{-c_{1,m}^+\exp(-k_0 w q_{1,m} z) + c_{1,m}^-\exp[k_0 q_{1,m}(z-d)]\}, \quad (A13a)$$

$$S_{xi}(z) = \sum_{m=1}^n w_{2,i,m}\{c_{2,m}^+\exp(-k_0 q_{2,m} z) + c_{2,m}^-\exp[k_0 q_{2,m}(z-d)]\}, \quad (A13b)$$

$$S_{yi}(z) = \sum_{m=1}^n v_{11,i,m}\{c_{1,m}^+\exp(-k_0 q_{1,m} z) + c_{1,m}^-\exp[k_0 q_{1,m}(z-d)]\} + \quad (A13c)$$

$$\sum_{m=1}^n v_{12,i,m}\{c_{2,m}^+ + \exp(-k_0 q_{2,m} z) + c_{2,m}^-\exp[k_0 q_{2,m}(z-d)]\},$$

$$U_{yi}(z) = \quad (A13d)$$

$$\sum_{m=1}^n v_{11,i,m}\{-c_{1,m}^+\exp(-k_0 q_{1,m} z) + c_{1,m}^-\exp[k_0 q_{1,m}(z-d)]\} +$$

$$\sum_{m=1}^n v_{22,i,m}\{-c_{2,m}^+\exp(-k_0 q_{2,m} z) + c_{2,m}^-\exp[k_0 q_{2,m}(z-d)]\},$$

Here $w_{1,i,m}$ and $q_{1,m}$ are the elements of the eigenvector matrix $W_1$ and the positive square root of the eigenvalues of the matrix $[K_y^2 I + A]$, respectively. The quantities $w_{2,i,m}$ and $q_{2,m}$ are the elements of the eigenvector matrix $W_2$ and the positive square root of the eigenvalues of the matrix $[K_y^2 I + BE]$, respectively. The quantities $v_{11,i,m}$, $v_{12,i,m}$, $v_{21,i,m}$ and $v_{22,i,m}$ are the elements of the matrices $V_{11}$, $V_{12}$, $V_{21}$ and $V_{22}$ that are given by $$V_{11} = A^{-1} W_1 Q_1$$

$$V_{12} = (k_y/k_0) A^{-1} K_x W_2$$

$$V_{21} = (k_y/k_0) B^{-1} K_x E^{-1} W_1$$

$$V_{22} = B^{-1} W_2 Q_2 \tag{A14}$$

where $Q_1$ and $Q_2$ are diagonal matrices with elements $q_{1,m}$ and $q_{2,m}$, respectively. The quantities $c_{1,m}^+$, $c_{1,m}^-$, $c_{2,m}^+$ and $c_{2,m}^-$ are unknown constants to be determined from the boundary conditions.

The boundary condition at z=0 can be expressed in the following matrix form:

$$\begin{bmatrix} \sin\psi \delta_{i0} \\ j\sin\psi n_I \cos\theta \delta_{i0} \\ -j\cos\psi n_I \delta_{i0} \\ \cos\psi \cos\theta \delta_{i0} \end{bmatrix} + \begin{bmatrix} I & 0 \\ -jY_I & 0 \\ 0 & I \\ 0 & -jZ_I \end{bmatrix} \begin{bmatrix} R_s \\ R_p \end{bmatrix} = \tag{A15}$$

$$\begin{bmatrix} V_{ss} & V_{sp} & V_{ss}X_1 & V_{sp}X_2 \\ W_{ss} & W_{sp} & -W_{ss}X_1 & -W_{sp}X_2 \\ W_{ps} & W_{pp} & -W_{ps}X_1 & -W_{pp}X_2 \\ V_{ps} & V_{pp} & V_{ps}X_1 & V_{pp}X_2 \end{bmatrix} \begin{bmatrix} C_1^+ \\ C_2^+ \\ C_1^- \\ C_2^- \end{bmatrix},$$

where $Y_I$ and $Z_I$ are diagonal matrices with elements $k_{I,zi}/k_0$ and $k_{I,zi}/(k_0 n_I^2)$, respectively. Here $$R_{s,i} = \cos\phi_i R_{yi} - \sin\phi_i R_{xi}$$

$$R_{p,i} = (-j/k_0)[\cos\phi_i(ik_{I,zi}R_{xi} - k_{xi}R_{zi}) - \sin\phi_i(k_y R_{zi} + k_{I,zi}R_{yi})] \tag{A16}$$

where $X_1$ and $X_2$ are diagonal matrices with elements $\exp(-k_0 q_{1,m} d)$ and $\exp(-k_0 q_{2,m} d)$, respectively, and $$V_{ss} = F_c V_{11}$$

$$W_{ss} = F_c W_1 + F_s V_{21}$$

$$V_{sp} = F_c V_{12} - F_s W_2$$

$$W_{sp} = F_s V_{22}$$

$$W_{pp} = F_c V_{22}$$

$$V_{pp} = F_c W_2 + F_s V_{12}$$

$$W_{ps} = F_c V_{21} - F_s W_1$$

$$V_{ps} = F_s V_{11} \tag{A17}$$

where $F_c$ and $F_s$ are diagonal matrices with the elements $\cos\phi_i$ and $\sin\phi_i$, respectively.

The boundary condition at z=d gives $$\begin{bmatrix} V_{ss}X_1 & V_{sp}X_2 & V_{ss} & V_{sp} \\ W_{ss}X_1 & W_{sp}X_2 & -W_{ss} & -W_{sp} \\ W_{ps}X_1 & W_{pp}X_2 & -W_{ps} & -W_{pp} \\ V_{ps}X_1 & V_{pp}X_2 & V_{ps} & V_{pp} \end{bmatrix} \cdot \begin{bmatrix} C_1^+ \\ C_2^+ \\ C_1^- \\ C_2^- \end{bmatrix} = \begin{bmatrix} I & 0 \\ jY_{II} & 0 \\ 0 & I \\ 0 & jZ_{II} \end{bmatrix} \cdot \begin{bmatrix} T_s \\ T_p \end{bmatrix}, \tag{A18}$$

where $Y_{II}$ and $Z_{II}$ are diagonal matrices with the elements $k_{II,zi}/k_0$ and $k_{II,zi}/(k_0 n_{II}^2)$, and $$T_{s,i} = \cos\phi_i T_{yi} - \sin\phi_i T_{xi}$$

$$T_{p,i} = (-j/k_0)[\cos\phi_i(k_{II,zi}T_{xi} - k_{xi}T_{zi}) - \sin\phi_i(-k_{II,zi}T_{yi} + k_y T_{zi})]. \tag{A19}$$

Based on Eqs. A15 and A12, the reflectance and transmittance for a given order i are given by $$DE_{ri} = |R_{s,i}|^2 Re\left(\frac{k_{I,zi}}{k_0 n_I \cos\theta}\right) + |R_{p,i}|^2 Re\left(\frac{k_{I,zi}/n_I^2}{k_0 n_I \cos\theta}\right) \tag{A20a}$$

$$DE_{ti} = |T_{s,i}|^2 Re\left(\frac{k_{II,zi}}{k_0 n_I \cos\theta}\right) + |T_{p,i}|^2 Re\left(\frac{k_{II,zi}/n_{II}^2}{k_0 n_I \cos\theta}\right) \tag{A20b}$$

APPENDIX A2

RCWA Normal Incident Plane ($\phi=0$)

In part 2 of this Appendix, results pertaining to the $\phi=0$ case (i.e., planar diffraction or normal incident plane) are given.

For normal incident plane (planar diffraction), the matrix eigenvalue problem corresponding to Eqs. All reduces to the simpler form given by $$\left[\frac{\partial^2 S_y}{\partial z^2}\right] = [A] \cdot [S_y], \text{ for } TE \tag{A21}$$

$$\left[\frac{\partial^2 S_y}{\partial z^2}\right] = [E_{Inv}^{-1} \cdot B] \cdot [S_y], \text{ for } TM$$

where matrices A and B are defined in Eq. A12, and $E_{inv}$ is the matrix formed by harmonic components of the inverse permittivity. Note that Eqs. A11 and A12 hold for arbitrary $\phi$, so they are used here to obtain $\phi=0$ results and above to obtain $\phi=\pi/2$ results. The matrices appearing within Eqs. A11 and A12 have $\phi$-dependent elements. In this case, the eigenproblem for $S_y$ is the same as for $U_x$, and for $U_y$ it is the same as for $S_x$ (as shown in JOSA, A 12, no. 5, p-1068-1076, 1995). The use of $E_{Inv}^{-1}$ is for improving numerical convergence, as described by P. Lalanne in JOSA, A 12, no. 4, p-779-784, 1996. The i,p element of $E_{inv}$ is equal to the Fourier coefficient $a_{i-p}$, where $$a(x) = \frac{1}{\varepsilon(x)} = \sum_{h=1}^{n} a_h \exp\left(j\frac{2\pi h}{\Lambda}\right), \quad (A22)$$

in general, and we have $$a_0 = \frac{f}{n_{rd}^2} + \frac{1-f}{n_{gr}^2}, \quad a_h = \left(\frac{1}{n_{rd}^2} - \frac{1}{n_{gr}^2}\right)\frac{\sin(\pi h f)}{\pi h}, \quad (A23)$$

for the Fourier components of the inverse permittivity of a binary grating as in FIG. 1. Note that the treatment of planar TM diffraction in Moharam et al. differs slightly from that given here, since Moharam et al. make use of the harmonic components of the permittivity for the TM case. Generally, an RCWA calculation can be done by expanding either the permittivity or the inverse permittivity in a Fourier series.

In this case the field expansions are given by $$S_{yi}(z) = \sum_{m=1}^{n} w_{i,m}\{c_m^+ \exp(-k_0 q_m z) + c_m^- \exp[k_0 q_m(z-d)]\}, \quad (A24a)$$

$$U_{xi}(z) = \sum_{m=1}^{n} v_{i,m}\{-c_{1,m}^+ + \exp(-k_0 w q_m z) + c_{1,m}^- \exp[k_0 q_m(z-d)]\},$$

TE mode $$U_{yi}(z) = \sum_{m=1}^{n} w_{i,m}\{c_m^+ \exp(-k_0 q_m z) + c_m^- \exp[k_0 q_m(z-d)]\} \quad (A24b)$$

$$S_{xi}(z) = \sum_{m=1}^{n} v_{i,m}\{-c_{1,m}^+ + \exp(-k_0 q_m z) + c_{1,m}^- \exp[k_0 q_m(z-d)]\},$$

TM mode

The boundary condition at z=0 is given by $$\begin{bmatrix} \delta_{i0} \\ jn_1\cos\theta \cdot \delta_{i0} \end{bmatrix} + \begin{bmatrix} I \\ -jY_I \end{bmatrix}[R] = \begin{bmatrix} W & WX \\ V & -VX \end{bmatrix}\begin{bmatrix} C^+ \\ C^- \end{bmatrix}, \text{ for } TE \quad (A25)$$

$$\begin{bmatrix} \delta_{i0} \\ j\cos\theta \cdot \delta_{i0}/n_1 \end{bmatrix} + \begin{bmatrix} I \\ -jZ_I \end{bmatrix}[R] = \begin{bmatrix} W & WX \\ V & -VX \end{bmatrix}\begin{bmatrix} C^+ \\ C^- \end{bmatrix}, \text{ for } TM.$$

The boundary condition at z=d is given by $$\begin{bmatrix} WX & W \\ VX & -V \end{bmatrix}\begin{bmatrix} C^+ \\ C^- \end{bmatrix} = \begin{bmatrix} I \\ -jY_{II} \end{bmatrix}[T], \text{ for } TE \quad (A26)$$

$$\begin{bmatrix} WX & W \\ VX & -V \end{bmatrix}\begin{bmatrix} C^+ \\ C^- \end{bmatrix} = \begin{bmatrix} I \\ -jZ_{II} \end{bmatrix}[T], \text{ for } TM.$$

Here R and T are the reflection and transmission coefficient vectors respectively, and $w_{i,m}$ and $q_m$ are the elements of the eigenvector matrix W and the positive square root of the eigenvalues of matrix A (for TE mode) or matrix $E_{inv}^{-1}B$ (for TM mode). We also have V=WQ, where Q is a diagonal matrix with the elements $q_m$. The matrices $Y_I$, $Y_{II}$, $Z_I$, $Z_{II}$ are as defined above following Eqs. A15 and A18.

For a normal incident angle ($\theta=0$) and a symmetric grating, the diffraction is symmetric. In this case, field components of the positive and negative diffraction orders are also symmetric, i.e., $S_{yi}=S_{y(-i)}$, $U_{xi}=U_{x(-i)}$, $R_i=R_{-i}$, $T_i=T_{-i}$. Matrix A with dimension 2N+1 in Eq. A21 can be simplified to the reduced N+1 dimension matrix $A^r$:

$$A_{i,j}^r = \begin{cases} A_{i,0}, & j=0 \\ A_{i,j} + A_{i,-j}, & j \neq 0 \end{cases} \quad (A27)$$

The same simplification can be applied to matrices B and $E_{inv}^{-1}$. So the dimension of the matrices formed by the eigenvalue-eigenvector (W) and related matrices (V, X) in Eqs. A25 and A26 are all reduced to N+1. The reflection and transmission coefficient vectors (R and T) are also reduced from 2N+1(−N, . . . , 0, . . . , N) to N+1 dimensions (0, . . . , N), in which only the zero and positive (or negative) diffraction orders are retained. Finally, the eigenvalue equation Eq. A21 and boundary conditions Eqs. A25, A25 keep the same form but with reduced matrices (and reduced dimension).

What is claimed is:

1. A system for optically determining one or more parameters of a substantially symmetric grating, the system comprising:
 a) an optical source providing optical radiation at a variable wavelength and illuminating said symmetric grating, wherein said radiation has a nonzero angle of incidence θ on said symmetric grating, and wherein a plane of incidence of said radiation is substantially parallel to lines of said symmetric grating;
 b) an optical detector receiving radiation from said symmetric grating and providing a measured spectral response; and
 c) a processor receiving said measured spectral response and providing a modeled spectral response of said symmetric grating having said parameters as variables, wherein said processor determines said one or more parameters by adjusting said variables to fit said modeled spectral response to said measured spectral response;
 wherein said modeled spectral response is provided by a symmetry-simplified analysis;
 wherein said symmetry-simplified analysis is a symmetry-simplified rigorous coupled wave (RCWA) analysis;
 wherein said symmetry-simplified RCWA comprises a symmetric RCWA for symmetric conical diffraction accounting for N positive and N negative diffraction orders using reduced matrices having dimension N+1;
 wherein R is one of said reduced matrices having a corresponding full matrix F, and wherein R is related to F as follows: $R_{i,j}=F_{i,j}+F_{i,-j}$ and $R_{i,0}=F_{i,0}$, where $0 \leq i \leq N$ and $1 \leq j \leq N$.

2. The system of claim 1, wherein said symmetry-simplified RCWA comprises a small incident angle RCWA for symmetric conical diffraction wherein polarization coupling is neglected.

3. The system of claim 2, wherein said optical radiation is s or p polarized.

4. The system of claim 1, wherein said symmetry-simplified RCWA comprises a normal incident angle RCWA.

5. The system of claim 4, wherein said grating separates region I having index $n_I$ from region II having index $n_{II}$, wherein said grating comprises two or more grating regions indexed by an integer i and having refractive indices $n_i$, and wherein said optical radiation is incident on said grating from said region I.

6. The system of claim 5, wherein said grating is a binary grating having lines and trenches with indices $n_1$ and $n_2$ respectively, and having a grating depth d and a trench index $n_2=n_I$, and wherein said normal incident angle RCWA comprises:
 calculating a propagation angle $\theta_1$ for said lines;
 calculating a revised depth $d'=d \cos \theta_1$ for said grating; and
 performing a normal incident angle RCWA using said revised depth d' instead of said depth d.

7. The system of claim 5, wherein said grating has a grating depth d, wherein said grating regions each have a filling factor $f_i$, and wherein said normal incident angle RCWA comprises:
 calculating a propagation angle $\theta_i$ in each of said grating regions;
 calculating an average propagation angle $\bar{\theta}$ for said grating according to $$\cos\bar{\theta} = \sum_i f_i \cdot \text{real}(n_i) \cdot \cos\theta_i / \sum_i f_i \cdot \text{real}(n_i);$$

calculating a revised depth $d'=d \cos \bar{\theta}$ for each of said grating regions; and
 performing a normal incident angle RCWA using said revised depth d' instead of said depth d.

8. The system of claim 5, wherein said optical radiation is p-polarized and wherein said normal incident angle RCWA comprises:
 calculating a propagation angle $\theta_i$ for each of said grating regions;
 calculating a propagation angle $\theta_{II}$ for said region II;
 calculating a revised index $n_i'=n_i \cos \theta_i$ for each of said grating regions;
 calculating a revised index $n_I'=n_I \cos \theta$ for said region I;
 calculating a revised index $n_{II}'=n_{II} \cos \theta_{II}$ for said region II; and
 performing a normal incident angle RCWA using said revised indices $n_I'$, $n_{II}'$, and $n_i'$, instead of $n_I$, $n_{II}$, and $n_i$ respectively.

9. The system of claim 1, wherein said symmetry-simplified RCWA comprises a planar diffraction RCWA calculation having revised indices or depths to account for plane wave components of said optical radiation which are not exactly in said plane of incidence.

10. The system of claim 1 wherein said grating is a single-layer non-binary grating.

11. The system of claim 1, wherein said grating is a multi-layer grating and wherein said symmetry-simplified RCWA comprises a multi-layer calculation.

12. The system of claim 11, wherein said multi-layer calculation comprises a partial calculation of the reflectances and not the transmittances.

13. The system of claim 1, wherein said optical radiation is s or p polarized.

14. The system of claim 1, wherein said parameters are selected from the group consisting of a line width, a grating period, a refractive index and a line depth.

15. The system of claim 1, wherein said measured spectral response is a measured spectral reflectance and said modeled spectral response is a modeled spectral reflectance.

16. The system of claim 1, wherein said measured spectral response is a measured spectral transmittance and said modeled spectral response is a modeled spectral transmittance.

17. The system of claim 1, wherein said measured spectral response is a measured zero order spectral response and said modeled spectral response is a modeled zero order spectral response.

18. A method for optically determining one or more parameters of a substantially symmetric grating, the method comprising:
 a) illuminating said symmetric grating with optical radiation, wherein said radiation has a nonzero angle of incidence $\theta$ on said symmetric grating, and wherein a plane of incidence of said radiation is substantially parallel to lines of said symmetric grating;
 b) providing a measured response of said symmetric grating by collecting radiation from said illuminated symmetric grating;
 c) providing a modeled response of said symmetric grating having said parameters as variables with a symmetry-simplified analysis; and
 d) determining said one or more parameters by adjusting said variables to fit said modeled response to said measured response;
 wherein said symmetry simplified analysis is a symmetry-simplified rigorous coupled-wave analysis (RCWA);
 wherein said symmetry-simplified RCWA comprises a symmetric RCWA for symmetric conical diffraction accounting for N positive and N negative diffraction orders using reduced matrices having dimension N+1;
 wherein R is one of said reduced matrices having a corresponding full matrix F, and wherein R is related to F as follows: $R_{i,j}=F_{i,j}+F_{i,-j}$ and $R_{i,0}=F_{i,0}$, where $0 \leq i \leq N$ and $1 \leq j \leq N$.

19. The method of claim 18, wherein said symmetry-simplified RCWA comprises a small incident angle RCWA for symmetric conical diffraction wherein polarization coupling is neglected.

20. The method of claim 19, wherein said optical radiation is s or p polarized.

21. The method of claim 18, wherein said symmetry-simplified RCWA comprises a normal incident angle RCWA.

22. The method of claim 21, wherein said grating separates region I having index $n_I$ from region II having index $n_{II}$, wherein said grating comprises two or more grating regions indexed by an integer i and having refractive indices $n_i$, and wherein said optical radiation is incident on said grating from said region I.

23. The method of claim 22, wherein said grating is a binary grating having lines and trenches with indices $n_1$ and $n_2$ respectively, and having a grating depth d and a trench index $n_2=n_I$, and wherein said normal incident angle RCWA comprises:
 calculating a propagation angle $\theta_1$ for said lines;
 calculating a revised depth $d'=d \cos \theta_1$ for said grating; and
 performing a normal incident angle RCWA using said revised depth d' instead of said depth d.

24. The method of claim 22, wherein said grating has a grating depth d, wherein each of said grating regions has a filling factor $f_i$, and wherein said normal incident angle RCWA comprises:
 calculating a propagation angle $\theta_i$ in each of said grating regions;
 calculating an average propagation angle $\bar{\theta}$ for said grating according to $$\cos\overline{\theta} = \sum_i f_i \cdot \text{real}(n_i) \cdot \cos\theta_i / \sum_i f_i \cdot \text{real}(n_i);$$

calculating a revised depth d'=d cos $\overline{\theta}$ for each of said grating regions; and performing a normal incident angle RCWA using said revised depth d' instead of said depth d.

25. The method of claim 22, wherein said optical radiation is p-polarized and wherein said normal incident angle RCWA comprises:

calculating a propagation angle $\theta_i$ for each of said grating regions;

calculating a propagation angle $\theta_{II}$ for said region II;

calculating a revised index $n_i'=n_i \cos\theta_i$ for each of said grating regions;

calculating a revised index $n_I'=n_I \cos\theta$ for said region I;

calculating a revised index $n_{II}'=n_{II} \cos\theta_{II}$ for said region II; and performing a normal incident angle RCWA using said revised indices $n_I'$, $n_{II}'$, and $n_i'$, instead of $n_I$, $n_{II}$, and $n_i$ respectively.

26. The method of claim 18, wherein said symmetry-simplified RCWA comprises a planar diffraction RCWA calculation having revised indices or depths to account for plane wave components of said optical radiation which are not exactly in said plane of incidence.

27. The method of claim 18 wherein said grating is a single-layer non-binary grating.

28. The method of claim 18, wherein said grating is a multi-layer grating and wherein said symmetry-simplified RCWA comprises a multi-layer calculation.

29. The method of claim 28, wherein said multi-layer calculation comprises a partial calculation of the reflectances and not the transmittances.

30. The method of claim 18, wherein said optical radiation is s or p polarized.

31. The method of claim 18, wherein said parameters are selected from the group consisting of a line width, a grating period, a refractive index and a line depth.

32. The method of claim 18, wherein said measured response is a measured reflectance and said modeled response is a modeled reflectance.

33. The method of claim 18, wherein said measured response is a measured transmittance and said modeled response is a modeled transmittance.

34. The method of claim 18, wherein said measured response is a measured spectral response and said modeled response is a modeled spectral response.

35. The method of claim 18, wherein said measured response is a measured zero order response and said modeled response is a modeled zero order response.

* * * * *